(12) United States Patent
Guenthenspberger et al.

(10) Patent No.: US 8,426,591 B2
(45) Date of Patent: Apr. 23, 2013

(54) 2-(SUBSTITUTED PHENYL)-6-AMINO-5-ALKOXY, THIOALKOXY AND AMINOALKYL-4-PYRIMIDINECARBOXYLATES AND THEIR USE AS HERBICIDES

(75) Inventors: Katherine A. Guenthenspberger, Daleville, IN (US); Thomas L. Siddall, Zionsville, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 279 days.

(21) Appl. No.: 12/623,833

(22) Filed: Nov. 23, 2009

(65) Prior Publication Data
US 2010/0121058 A1    May 13, 2010

Related U.S. Application Data

(62) Division of application No. 12/200,945, filed on Aug. 29, 2008, now Pat. No. 7,642, 220.

(60) Provisional application No. 60/966,877, filed on Aug. 30, 2007, provisional application No. 61/067,128, filed on Feb. 26, 2008.

(51) Int. Cl.
*C07D 239/52* (2006.01)
(52) U.S. Cl.
USPC .......................................... 544/319
(58) Field of Classification Search ............ 544/319
See application file for complete search history.

(56) References Cited

U.S. PATENT DOCUMENTS

| 7,300,907 | B2 | 11/2007 | Epp et al. |
| 2009/0048109 | A1 | 2/2009 | Epp et al. |
| 2009/0088322 | A1 | 4/2009 | Epp et al. |

FOREIGN PATENT DOCUMENTS

| WO | PCT/2005/063721 | 7/2005 |
| WO | PCT/US2007/082076 | 7/2007 |
| WO | PCT/US2008/074702 | 12/2008 |

OTHER PUBLICATIONS

Liu et al., CAPLUS Abstract 130:168426 (1999).*
Liu et al., Studies on Bio-rational Design of Photosystem II Inhibitors, Gaodeng Xuexiao Huaxue Xuebao (1998), 19(12), pp. 1946-1949.*
Vincenzo Summa, Alessia Petrocci, Victor G. Matassa, Marina Taliani, Ralph Laufer, Raffaele De Francesco, Sergio Altamura and Paola Pace; HCV NS5b RNA-Dependent RNA Polymerase Inhibitors: From r,ç-Diketoacids to 4,5-Dihydroxypyrimidine- or 3-Methyl-5-hydroxypyrimidinonecarboxylic Acids. Design and Synthesis, Jul. 5, 2004; J. Med. Chem. 2004, 47, 5336-5339; 2004 American Chemical Society, Published on Web Sep. 16, 2004.
Vincenzo Summa, Alessia Petrocci, Victor G. Matassa, Marina Taliani, Ralph Laufer, Raffaele De Francesco, Sergio Altamura and Paola Pace; HCV NS5b RNA-Dependent RNA Polymerase Inhibitors: From r,ç-Diketoacids to 4,5-Dihydroxypyrimidine- or 3-Methyl-5-hydroxypyrimidinonecarboxylic Acids. Design and Synthesis; Supporting Information; S 1-S 6, J. Med. Chem. 2004, 47.

* cited by examiner

*Primary Examiner* — Deepak Rao
(74) *Attorney, Agent, or Firm* — Rob Chang

(57) ABSTRACT

2-(Substituted phenyl)-6-amino-5-alkoxy, thioalkoxy and aminoalkyl-4-pyrimidinecarboxylic acid and its derivatives are potent herbicides demonstrating broad spectrum of weed control.

5 Claims, No Drawings

2-(SUBSTITUTED PHENYL)-6-AMINO-5-ALKOXY, THIOALKOXY AND AMINOALKYL-4-PYRIMIDINECARBOXYLATES AND THEIR USE AS HERBICIDES

This application is a divisional of U.S. application Ser. No. 12/200,945 filed Aug. 29, 2008 and claims priority from U.S. provisional applications 60/966,877 filed Aug. 30, 2007 and 61/067,128 filed Feb. 26, 2008.

BACKGROUND OF THE INVENTION

This invention relates to 2-(substituted phenyl)-6-amino-5-alkoxy, thioalkoxy and aminoalkyl-4-pyrimidinecarboxylic acids and their derivatives and to the use of these compounds as herbicides.

A number of pyrimidinecarboxylic acids and their pesticidal properties have been described in the art. WO 2005/063721 A1, WO 2007/082076 A1, and U.S. Pat. No. 7,300,907 (B2) generically disclose 2-substituted-6-amino-4-pyrimidine-carboxylic acids and their derivatives and their use as herbicides. It has now been discovered that certain particular subclasses of the compounds disclosed in '721 have greatly improved herbicidal activity and selectivity.

SUMMARY OF THE INVENTION

It has now been found that 2-(substituted phenyl)-6-amino-5-alkoxy, thioalkoxy and aminoalkyl-4-pyrimidinecarboxylic acids and their derivatives are superior herbicides with a broad spectrum of weed control against broadleaf weeds as well as grass and sedge weeds and with excellent crop selectivity at low use rates. The compounds further possess excellent toxicological or environmental profiles.

The invention includes compounds of Formula I:

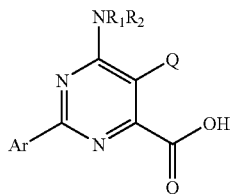

I wherein

Q represents a $C_1$-$C_4$ alkoxy, $C_1$-$C_4$ haloalkoxy, $C_1$-$C_4$ thioalkoxy, $C_1$-$C_4$ halothioalkoxy or —$NR_3R_4$;

$R_1$ and $R_2$ independently represent H, $C_1$-$C_6$ alkyl, $C_3$-$C_6$ alkenyl, $C_3$-$C_6$ alkynyl, hydroxy, $C_1$-$C_6$ alkoxy, amino, $C_1$-$C_6$ acyl, $C_1$-$C_6$ carboalkoxy, $C_1$-$C_6$ alkylcarbamyl, $C_1$-$C_6$ alkylsulfonyl, $C_1$-$C_6$ trialkylsilyl or $C_1$-$C_6$ dialkyl phosphonyl or $R_1$ and $R_2$ taken together with N represent a 5- or 6-membered saturated ring;

Ar represents a phenyl group substituted with one to four substitutents selected from halogen, nitro, cyano, formyl, $C_1$-$C_6$ alkyl, $C_2$-$C_6$ alkenyl, $C_2$-$C_6$ alkynyl, $C_1$-$C_6$ alkoxy, $C_2$-$C_4$ alkoxyalkyl, $C_2$-$C_6$ alkylcarbonyl, $C_1$-$C_6$ alkylhio, $C_1$-$C_6$ alkylsulfinyl, $C_1$-$C_6$ alkylsulfonyl, $C_2$-$C_4$ alkenyloxy, $C_2$-$C_4$ alkynloxy, $C_2$-$C_4$ alkenylthio, $C_2$-$C_4$ alkynylthio, $C_1$-$C_6$ haloalkyl, $C_2$-$C_6$ haloalkenyl, $C_2$-$C_6$ haloalkynyl, $C_1$-$C_6$ haloalkoxy, $C_2$-$C_4$ haloalkoxyalkyl, $C_2$-$C_6$ haloalkylcarbonyl, $C_1$-$C_6$ haloalkylthio, $C_1$-$C_6$ haloalkylsulfinyl, $C_1$-$C_6$ haloalkylsulfonyl, $C_3$-$C_6$ trialkylsilyl, $C_2$-$C_4$ haloalkenyloxy, $C_2$-$C_4$ haloalkynyloxy, $C_2$-$C_4$ haloalkenylthio, $C_2$-$C_4$ haloalkynylthio, —$OCH_2CH_2$—, —$OCH_2CH_2CH_2$—, —$OCH_2$—O—, —$OCH_2CH_2$—O—, —C(O)$OR_4$, —C(O)$NR_3R_4$, —$CR_3NOR_4$, —$NR_3R_4$, —$NR_3OR_4$, —$NR_3SO_2R_4$, —$NR_3C(O)R_4$, —$NR_3C(O)OR_4$, —$NR_3C(O)NR_3R_4$ or —$NCR_3NR_3R_4$;

$R_3$ represents H, $C_1$-$C_4$ alkyl or $C_1$-$C_4$ haloalkyl; and
$R_4$ represents $C_1$-$C_4$ alkyl or $C_1$-$C_4$ haloalkyl;
and agriculturally acceptable derivatives of the carboxylic acid group.

Preferred compounds of formula (I) independently include those in which Ar represents para-substituted phenyl with or without other substituents, wherein Q represents methoxy, halomethoxy, thiomethoxy or halothiomethoxy and wherein $R_1$ and $R_2$ independently represent H or $C_1$-$C_6$ alkyl, with both $R_1$ and $R_2$ represent H being most preferred.

The invention includes herbicidal compositions comprising an herbicidally effective amount of a compound of Formula I and agriculturally acceptable derivatives of the carboxylic acid group in admixture with an agriculturally acceptable adjuvant or carrier. The invention also includes a method of use of the compounds and compositions of the present invention to kill or control undesirable vegetation by application of an herbicidal amount of the compound to the vegetation or to the locus of the vegetation as well as to the soil prior to emergence of the vegetation.

DETAILED DESCRIPTION OF THE INVENTION

The herbicidal compounds of the present invention are derivatives of 2-(substituted phenyl)-6-amino-5-alkoxy, thioalkoxy and aminoalkyl-4-pyrimidinecarboxylic acid:

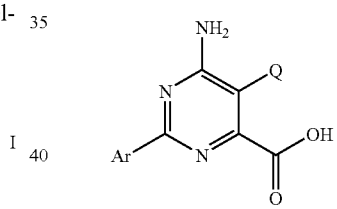

wherein

Q represents a $C_1$-$C_4$ alkoxy, $C_1$-$C_4$ haloalkoxy, $C_1$-$C_4$ thioalkoxy, $C_1$-$C_4$ halothioalkoxy or —$NR_3R_4$;

Ar represents a phenyl group substituted with one or more substitutents selected from halogen, nitro, cyano, formyl, $C_1$-$C_6$ alkyl, $C_2$-$C_6$ alkenyl, $C_2$-$C_6$ alkynyl, $C_1$-$C_6$ alkoxy, $C_2$-$C_4$ alkoxyalkyl, $C_2$-$C_6$ alkylcarbonyl, $C_1$-$C_6$ alkylhio, $C_1$-$C_6$ alkylsulfinyl, $C_1$-$C_6$ alkylsulfonyl, $C_2$-$C_4$ alkenyloxy, $C_2$-$C_4$ alkynloxy, $C_2$-$C_4$ alkenylthio, $C_2$-$C_4$ alkynylthio, $C_1$-$C_6$ haloalkyl, $C_2$-$C_6$ haloalkenyl, $C_2$-$C_6$ haloalkynyl, $C_1$-$C_6$ haloalkoxy, $C_2$-$C_4$ haloalkoxyalkyl, $C_2$-$C_6$ haloalkylcarbonyl, $C_1$-$C_6$ haloalkylthio, $C_1$-$C_6$ haloalkylsulfinyl, $C_1$-$C_6$ haloalkylsulfonyl, $C_3$-$C_6$ trialkylsilyl, $C_2$-$C_4$ haloalkenyloxy, $C_2$-$C_4$ haloalkynyloxy, $C_2$-$C_4$ haloalkenylthio, $C_2$-$C_4$ haloalkynylthio, —$OCH_2CH_2$—, —$OCH_2CH_2CH_2$—, —$OCH_2$—O—, —$OCH_2CH_2$—O—, C(O)$OR_4$, —C(O)$NR_3R_4$, —$CR_3NOR_4$, —$NR_3R_4$, —$NR_3OR_4$, —$NR_3SO_2R_4$, —$NR_3C(O)R_4$, —$NR_3C(O)OR_4$, —$NR_3C(O)NR_3R_4$ or —$NCR_3NR_3R_4$;

$R_3$ represents H, $C_1$-$C_4$ alkyl or $C_1$-$C_4$ haloalkyl; and
$R_4$ represents $C_1$-$C_4$ alkyl or $C_1$-$C_4$ haloalkyl.

The amino group at the 6-position of the pyrimidine ring can be unsubstituted or substituted with one or more $C_1$-$C_6$ alkyl, $C_3$-$C_6$ alkenyl, $C_3$-$C_6$ alkynyl, hydroxy, $C_1$-$C_6$ alkoxy or amino substituents. The amino group can be further derivatized as an amide, a carbamate, a urea, a sulfonamide, a silylamine or a phosphoramidate. Such derivatives are capable of breaking down into the amine. An unsubstituted amino group or one substituted with one or two alkyl substituents is preferred.

The carboxylic acids of Formula I are believed to be the compounds that actually kill or control undesirable vegetation and are typically preferred. Analogs of these compounds in which the acid group of the pyrimidine carboxylic acid is derivatized to form a related substituent that can be transformed within plants or the environment to an acid group possess essentially the same herbicidal effect and are within the scope of the invention. Therefore, an "agriculturally acceptable derivative", when used to describe the carboxylic acid functionality at the 4-position, is defined as any salt, ester, acylhydrazide, imidate, thioimidate, amidine, amide, orthoester, acylcyanide, acyl halide, thioester, thionoester, dithiolester, nitrile or any other acid derivative well known in the art which (a) does not substantially affect the herbicidal activity of the active ingredient, i.e., the 2-(substituted phenyl)-6-amino-5-alkoxy, thioalkoxy and aminoalkyl-4-pyrimidine-carboxylic acid, and (b) is or can be hydrolyzed, oxidized or metabolized in plants or soil to the 2-(substituted phenyl)-6-amino-5-alkoxy, thioalkoxy and aminoalkyl-4-pyrimidinecarboxylic acid that, depending upon the pH, is in the dissociated or the undissociated form. The preferred agriculturally acceptable derivatives of the carboxylic acid are agriculturally acceptable salts, esters and amides. Likewise, an "agriculturally acceptable derivative", when used to describe the amine functionality at the 6-position, is defined as any salt, silylamine, phosphorylamine, phosphinimine, phosphoramidate, sulfonamide, sulfilimine, sulfoximine, aminal, hemiaminal, amide, thioamide, carbamate, thiocarbamate, amidine, urea, imine, nitro, nitroso, azide, or any other nitrogen containing derivative well known in the art which (a) does not substantially affect the herbicidal activity of the active ingredient, i.e., the 2-(substituted phenyl)-6-amino-5-alkoxy, thioalkoxy and aminoalkyl-4-pyrimidinecarboxylic acid, and (b) is or can be hydrolyzed in plants or soil to a free amine N-Oxides which are also capable of breaking into the parent pyrimidine are also covered by the scope of this invention.

Suitable salts include those derived from alkali or alkaline earth metals and those derived from ammonia and amines. Preferred cations include sodium, potassium, magnesium, and aminium cations of the formula:

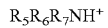

wherein $R_5$, $R_6$ and $R_7$ each, independently represents hydrogen or $C_1$-$C_{12}$ alkyl, $C_3$-$C_{12}$ alkenyl or $C_3$-$C_{12}$ alkynyl, each of which is optionally substituted by one or more hydroxy, $C_1$-$C_4$ alkoxy, $C_1$-$C_4$ alkylthio or phenyl groups, provided that $R_5$, $R_6$, and $R_7$ are sterically compatible. Additionally, any two of $R_5$, $R_6$, and $R_7$ together may represent an aliphatic difunctional moiety containing 1 to 12 carbon atoms and up to two oxygen or sulfur atoms. Salts of the compounds of Formula I can be prepared by treatment of compounds of Formula I with a metal hydroxide, such as sodium hydroxide, or an amine, such as ammonia, trimethylamine, diethanolamine, 2-methylthiopropylamine, bisallylamine, 2-butoxyethylamine, morpholine, cyclododecylamine, or benzylamine Amine salts are often preferred forms of the compounds of Formula I because they are water-soluble and lend themselves to the preparation of desirable aqueous based herbicidal compositions.

Suitable esters include those derived from $C_1$-$C_{12}$ alkyl, $C_3$-$C_{12}$ alkenyl or $C_3$-$C_{12}$ alkynyl alcohols, such as methanol, iso-propanol, butanol, 2-ethylhexanol, butoxyethanol, methoxypropanol, allyl alcohol, propargyl alcohol or cyclohexanol. Esters can be prepared by coupling of the 2-(substituted phenyl)-6-amino-5-alkoxy, thioalkoxy and aminoalkyl-4-pyrimidinecarboxylic acid with the alcohol using any number of suitable activating agents such as those used for peptide couplings such as dicyclohexylcarbodiimide (DCC) or carbonyl diimidazole (CDI), by reacting the corresponding acid chloride of 2-(substituted phenyl)-6-amino-5-alkoxy, thioalkoxy and aminoalkyl-4-pyrimidinecarboxylic acid with an appropriate alcohol, by reacting the 2-(substituted phenyl)-6-amino-5-alkoxy, thioalkoxy and aminoalkyl-4-pyrimidinecarboxylic acid with an appropriate alcohol in the presence of an acid catalyst or by transesterification. Suitable amides include those derived from ammonia or from $C_1$-$C_{12}$ alkyl, $C_3$-$C_{12}$ alkenyl or $C_3$-$C_{12}$ alkynyl mono- or di-substituted amines, such as but not limited to dimethylamine, diethanolamine, 2-methylthiopropylamine, bisallylamine, 2-butoxyethylamine, cyclododecylamine, benzylamine or cyclic or aromatic amines with or without additional heteroatoms such as but not limited to aziridine, azetidine, pyrrolidine, pyrrole, imidazole, tetrazole or morpholine. Amides can be prepared by reacting the 2-(substituted phenyl)-6-amino-5-alkoxy, thioalkoxy and aminoalkyl-4-pyrimidine-carboxylic acid chloride, mixed anhydride, or carboxylic ester of Formula I with ammonia or an appropriate amine.

The terms "alkyl", "alkenyl" and "alkynyl", as well as derivative terms such as "alkoxy", "acyl", "alkylthio" and "alkylsulfonyl", as used herein, include within their scope straight chain, branched chain and cyclic moieties. The terms "alkenyl" and "alkynyl" are intended to include one or more unsaturated bonds.

The term "thioalkoxy," as used herein, refers to an —S-alkyl group, also referred to as an alkylthio or an alkylsulfanyl group.

Unless specifically limited otherwise, the term "halogen" including derivative terms such as "halo" refers to fluorine, chlorine, bromine, and iodine.

Phenyl groups may be substituted with from one to four substituents, provided the substituents are sterically compatible and the rules of chemical bonding and strain are satisfied.

The compounds of Formula I can be made using well-known chemical procedures. Many procedural details for making compounds of Formula I can be found in the following patent applications: WO 2007/082076 A1 and WO 2005/063721 A1. Intermediates not specifically mentioned herein or in the above patent applications are either commercially available, can be made by routes disclosed in the chemical literature, or can be readily synthesized from commercial starting materials utilizing standard procedures.

As shown in Scheme 1, the 2-(substituted phenyl)-6-amino-5-alkoxy, thioalkoxy and aminoalkyl-4-pyrimidinecarboxylic acid esters of Formula I can be prepared by reaction of an appropriately substituted pyrimidine of type II and an organometallic compound of type III in an inert solvent in the presence of a transition metal catalyst.

Scheme 1

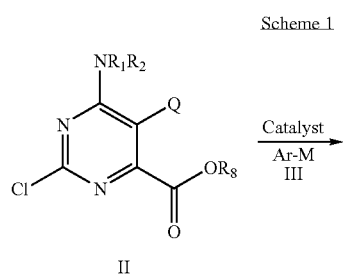

In this case Q can be alkoxy, haloalkoxy, thioalkoxy, halothioalkoxy, alkylamino or haloalkylamino; $R_8$ can be alkyl; M can be tri-($C_1$-$C_4$ alkyl)tin or B(O$R_9$)(O$R_{10}$), where $R_9$ and $R_{10}$ are independently of one another, hydrogen, $C_1$-$C_6$ alkyl, or when taken together form an ethylene or propylene group; and "Catalyst" can be a transition metal catalyst, in particular a palladium catalyst such as bis(triphenylphosphine)palladium(II) dichloride. The method of Scheme 1 is illustrated in Example 12.

As shown in Scheme 2, appropriately substituted pyrimidines of Formula II can be prepared by reaction of pyrimidines of type IV (see *J. Med. Chem.* 49(5), 1693-1705; 2006 for preparation of 2,6-dichloro-5-methoxy-pyrimidine-4-carboxylic acid methyl ester) with amines of type V. In this case, Q can be alkoxy, haloalkoxy, thioalkoxy, halothioalkoxy, alkylamino or haloalkylamino; and $R_8$ can be alkyl. The method of Scheme 2 is illustrated in Example 9.

Scheme 2

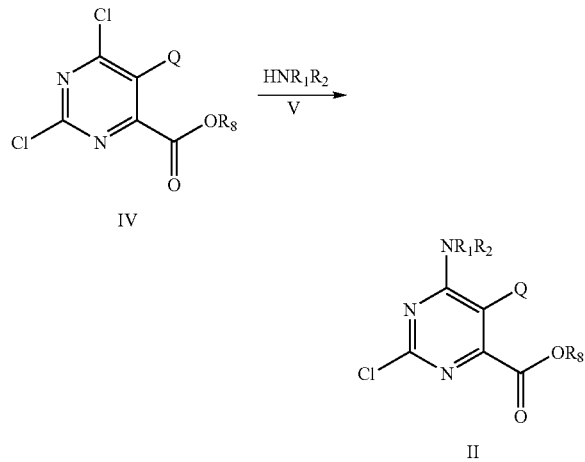

Alternatively, as shown in Scheme 3, appropriately substituted pyrimidines of Formula II can be prepared by reaction of pyrimidines of type VII (see U.S. Pat. No. 3,984,411 for the preparation of 2,4,6-trichloro-5-methoxypyrimidine and FR 1549494 for the preparation of 2,4,6-trichloro-5-methylsulfanylpyrimidine) with amines of type V; followed by reaction of type VI pyrimidines with carbon monoxide in a solvent such as ethanol in the presence of a transition metal catalyst. In this case, Q can be alkoxy, haloalkoxy, thioalkoxy, halothioalkoxy, alkylamino or haloalkylamino; $R_8$ can be alkyl; and "Catalyst" can be a transition metal catalyst such as that formed by the combination of palladium acetate and 1,4-bis(diphenylphosphino)butane (DPPB). The methods of Scheme 3 are illustrated in Examples 10 and 11.

Scheme 3

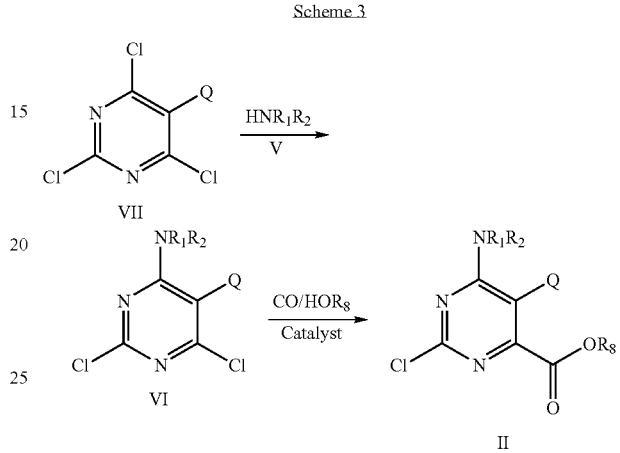

As shown in Scheme 4, the 2-(substituted phenyl)-6-amino-5-alkoxy, thioalkoxy and aminoalkyl-4-pyrimidinecarboxylic acid esters of Formula I can also be made by reaction of pyrimidines of type IX with amines of type V; followed by reaction of type VIII pyrimdines with carbon monoxide in a solvent such as methanol in the presence of a transition metal catalyst. In this case, Q can be alkoxy or haloalkoxy, thioalkoxy, halothioalkoxy, alkylamino or haloalkylamino; $R_8$ can be alkyl; and "Catalyst" can be a transition metal catalyst such as that formed by the combination of palladium acetate and DPPB. The methods of Scheme 4 are illustrated in Examples 17 and 18.

Scheme 4

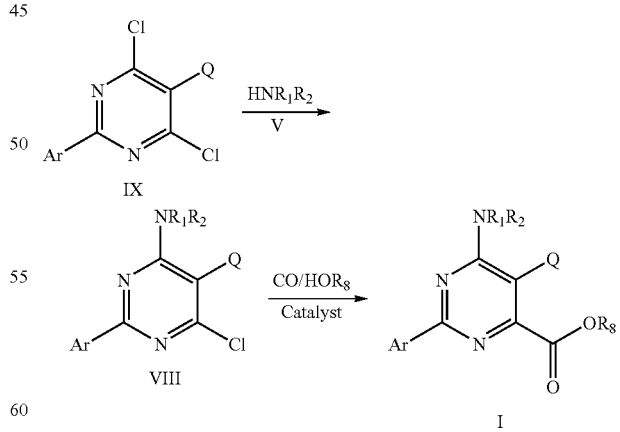

As shown in Scheme 5, appropriately substituted pyrimidines of Formula IX can be made by reaction of amidines of type XII with compounds of type XI in the presence of a base such as sodium methoxide in a solvent such as methanol; followed by reaction of type X pyrimidines with a chlorinating agent such as phosphorous oxychloride in the presence of N,N-dimethylaniline 1n this case, Q can be alkoxy or haloalkoxy, thioalkoxy, halothioalkoxy, alkylamino or haloalkylamino; and $R_8$ can be alkyl. The methods of Scheme 5 are illustrated in Example 16.

Scheme 5

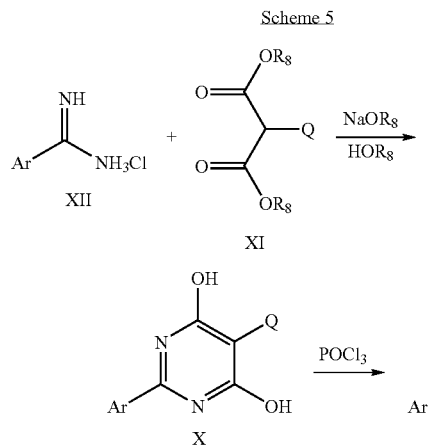

As shown in Scheme 6, the 2-(substituted phenyl)-6-amino-5-alkoxy, thioalkoxy and aminoalkyl-4-pyrimidinecarboxylic acids of Formula I can also be made by hydrolysis of pyrimidines of type XIV; followed by reaction with a chlorinating agent such as thionyl chloride in the presence of a catalyst such as dimethyl formamide (DMF) in a solvent such as ethyl acetate; followed by reaction of type XIII pyrimidines with amines of type V. In this case, Q can be alkoxy or haloalkoxy, thioalkoxy, halothioalkoxy, alkylamino or haloalkylamino; and $R_8$ can be alkyl. The methods of Scheme 6 are illustrated in Examples 20 and 21.

Scheme 6

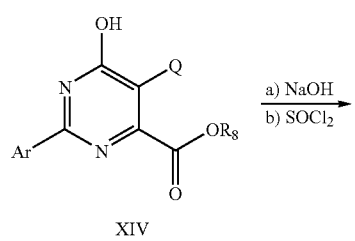

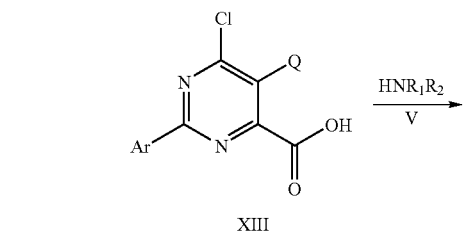

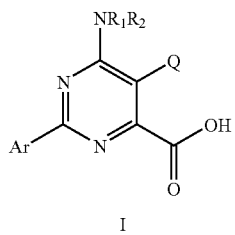

As shown in Scheme 7, appropriately substituted pyrimidines of Formula XIV can be made by reaction of amidines of type XII with compounds of type XV in the presence of a base such as sodium methoxide in a solvent such as methanol. In this case, Q can be alkoxy or haloalkoxy, thioalkoxy, halothioalkoxy, alkylamino or haloalkylamino; and $R_8$ can be alkyl. The method of Scheme 7 is illustrated in Example 19.

Scheme 7

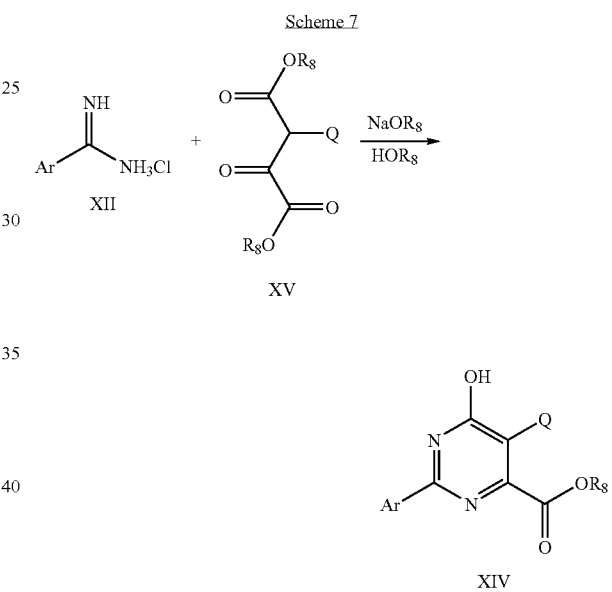

As shown in Scheme 8, the 2-(substituted phenyl)-6-amino-5-thioalkoxy-4-pyrimidinecarboxylic acid esters of Formula I can be prepared by reaction of an appropriately substituted pyrimidine of type XVI with a sodium thiolate salt of type XVII in the presence of cuprous iodide in a polar aprotic solvent such as DMF. In this case $R_{11}$ can be alkyl or haloalkyl and Q can be thioalkoxy or halothioalkoxy. The method of Scheme 8 is illustrated in Example 22.

Scheme 8

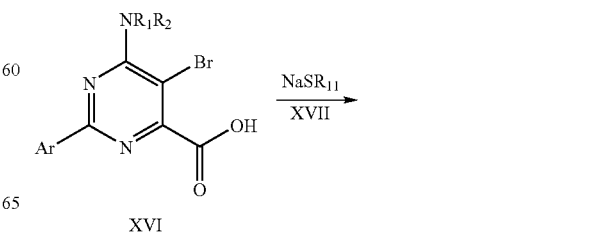

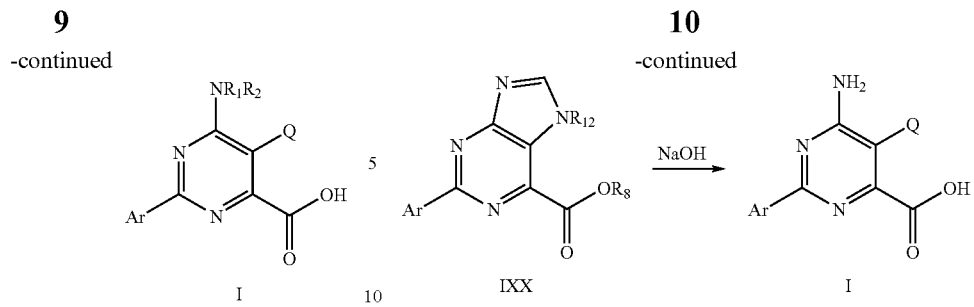

As shown in Scheme 9, the 2-(substituted phenyl)-6-amino-5-haloalkoxy-4-pyrimidinecarboxylic acid esters of Formula I can be prepared by reaction of an appropriately substituted pyrimidine of type XVI with an alcohol of type XVIII in the presence of cuprous iodide in a polar aprotic solvent such as DMF. In this case $R_{11}$ can be haloalkyl and Q can be haloalkoxy. The method of Scheme 9 is illustrated in Example 23.

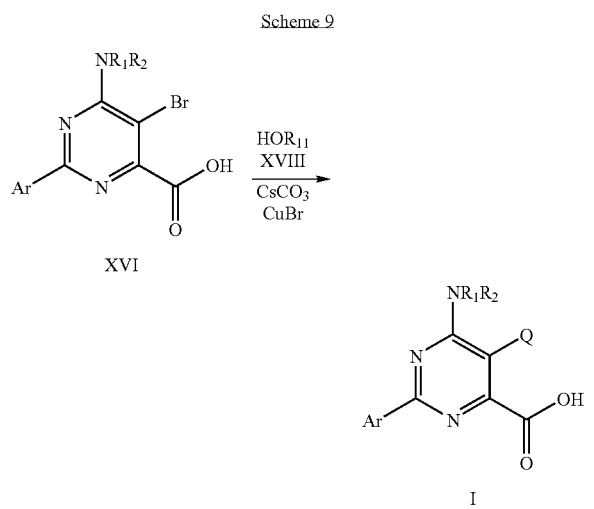

As shown in Scheme 10, the 2-(substituted phenyl)-6-amino-5-alkylamino-4-pyrimidinecarboxylic acids of Formula I can be prepared by reaction of an appropriately substituted purine of type XX with carbon monoxide in a solvent such as methanol in the presence of a transition metal catalyst; followed by hydrolysis of type IXX purines with a base such as sodium hydroxide in solvent such as water. In this case $R_{12}$ can be alkyl or haloalkyl; Q can be aminoalkyl or haloaminoalkyl; and "Catalyst" can be a transition metal catalyst such as that formed by the combination of palladium acetate and DPPB. The methods of Scheme 10 are illustrated in Examples 27 and 28.

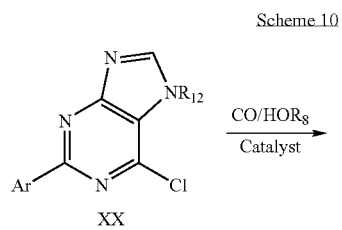

As shown in Scheme 11, appropriately substituted purines of Formula XX can be made by heating purines of type XXI. with hydrochloric acid in water; followed by reaction with a chlorinating agent such as thionyl chloride with a catalyst such as DMF in a solvent such as chloroform. In this case, $R_{12}$ can be alkyl or haloalkyl. The methods of Scheme 11 are illustrated in Example 26.

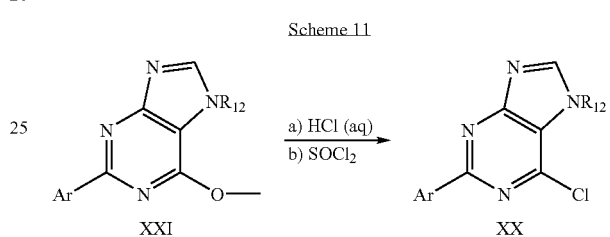

As shown in Scheme 12, appropriately substituted purines of Formula XXI can be prepared by reaction of an appropriately substituted purine of type XXII (see Monatshefte fuer Chemie (1985), 116(3), 341-51 for preparation of 2-chloro-6-methoxy-7-methyl-7H-purine) and an organometallic compound of type III in an inert solvent in the presence of a transition metal catalyst.

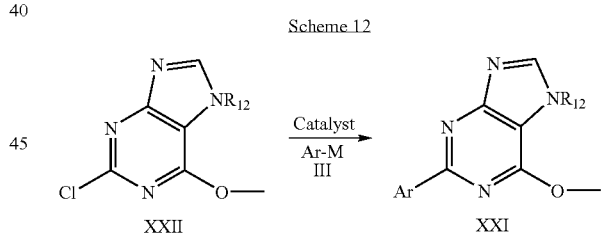

In this case $R_{12}$ can be alkyl or haloalkyl; M can be tri-($C_1$-$C_4$ alkyl)tin or $B(OR_9)(OR_{10})$, where $R_9$ and $R_{10}$ are independently of one another, hydrogen, $C_1$-$C_6$ alkyl, or when taken together form an ethylene or propylene group; and "Catalyst" can be a transition metal catalyst, in particular a palladium catalyst such as bis(triphenylphosphine)-palladium(II) dichloride. The method of Scheme 12 is illustrated in Example 25.

It is recognized that some reagents and reaction conditions disclosed herein or in the chemical literature for preparing compounds of Formula I may not be compatible with certain functionalities present in the intermediates. In these instances, the incorporation of protection/deprotection sequences or functional group interconversions into the synthesis will aid in obtaining the desired products. The use and choice of the protection groups will be apparent to one skilled in chemical synthesis.

One skilled in the art will recognize that, in some cases, after the introduction of a given reagent as disclosed herein or in the chemical literature, it may be necessary to perform additional routine synthetic steps not described in detail to complete the synthesis of compounds of Formula I. One skilled in the art will also recognize that it may necessary to perform a combination of the steps disclosed herein or in the chemical literature in an order other than that implied by the particular sequence presented to prepare the compounds of Formula I.

Finally, one skilled in the art will also recognize that compounds of Formula I and the intermediates described herein or in the chemical literature can be subjected to various electrophilic, nucleophilic, radical, organometallic, oxidation, and reduction reactions to add substituents or modify existing substituents.

The compounds of Formula I have been found to be useful as pre-emergence and post-emergence herbicides. They can be employed at non-selective (higher) rates of application to control a broad spectrum of the vegetation in an area or at lower rates of application for the selective control of undesirable vegetation. Areas of application include pasture and rangelands, roadsides and rights of way, power lines and any industrial areas where control of undesirable vegetation is desirable. Another use is the control of unwanted vegetation in crops such as corn, rice and cereals. They can also be used to control undesirable vegetation in tree crops such as citrus, apple, rubber, oil palm, forestry and others. It is usually preferred to employ the compounds postemergence. It is further usually preferred to use the compounds to control a wide spectrum of woody plants, broadleaf and grass weeds, and sedges. Use of the compounds to control undesirable vegetation in established crops is especially indicated. While each of the 2-(substituted phenyl)-6-amino-5-alkoxy, thioalkoxy and aminoalkyl-4-pyrimidinecarboxylate compounds encompassed by Formula I is within the scope of the invention, the degree of herbicidal activity, the crop selectivity, and the spectrum of weed control obtained varies depending upon the substituents present. An appropriate compound for any specific herbicidal utility can be identified by using the information presented herein and routine testing.

The term herbicide is used herein to mean an active ingredient that kills, controls or otherwise adversely modifies the growth of plants. An herbicidally effective or vegetation controlling amount is an amount of active ingredient which causes an adversely modifying effect and includes deviations from natural development, killing, regulation, desiccation, retardation, and the like. The terms plants and vegetation include germinant seeds, emerging seedlings and established vegetation.

Herbicidal activity is exhibited by the compounds of the present invention when they are applied directly to the plant or to the locus of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, it is preferred to apply the compounds of Formula I postemergence to relatively immature undesirable vegetation to achieve the maximum control of weeds.

Application rates of about 1 to about 1,000 g/Ha are generally employed in postemergence operations; for preemergence applications, rates of about 10 to about 2,000 g/Ha are generally employed. The higher rates designated generally give non-selective control of a broad variety of undesirable vegetation. The lower rates typically give selective control and can be employed in the locus of crops.

The herbicidal compounds of the present invention are often applied in conjunction with one or more other herbicides to control a wider variety of undesirable vegetation. When used in conjunction with other herbicides, the presently claimed compounds can be formulated with the other herbicide or herbicides, tank mixed with the other herbicide or herbicides or applied sequentially with the other herbicide or herbicides. Some of the herbicides that can be employed in conjunction with the compounds of the present invention include: amide herbicides such as allidochlor, beflubutamid, benzadox, benzipram, bromobutide, cafenstrole, CDEA, chlorthiamid, cyprazole, dimethenamid, dimethenamid-P, diphenamid, epronaz, etnipromid, fentrazamide, flupoxam, fomesafen, halosafen, isocarbamid, isoxaben, napropamide, naptalam, pethoxamid, propyzamide, quinonamid and tebutam; anilide herbicides such as chloranocryl, cisanilide, clomeprop, cypromid, diflufenican, etobenzanid, fenasulam, flufenacet, flufenican, mefenacet, mefluidide, metamifop, monalide, naproanilide, pentanochlor, picolinafen and propanil; arylalanine herbicides such as benzoylprop, flampropand flamprop-M; chloroacetanilide herbicides such as acetochlor, alachlor, butachlor, butenachlor, delachlor, diethatyl, dimethachlor, metazachlor, metolachlor, S-metolachlor, pretilachlor, propachlor, propisochlor, prynachlor, terbuchlor, thenylchlor and xylachlor; sulfonanilide herbicides such as benzofluor, perfluidone, pyrimisulfan and profluazol; sulfonamide herbicides such as asulam, carbasulam, fenasulam and oryzalin; antibiotic herbicides such as bilanafos; benzoic acid herbicides such as chloramben, dicamba, 2,3,6-TBA and tricamba; pyrimidinyloxybenzoic acid herbicides such as bispyribac and pyriminobac; pyrimidinylthiobenzoic acid herbicides such as pyrithiobac; phthalic acid herbicides such as chlorthal; picolinic acid herbicides such as aminopyralid, clopyralid and picloram; quinolinecarboxylic acid herbicides such as quinclorac and quinmerac; arsenical herbicides such as cacodylic acid, CMA, DSMA, hexaflurate, MAA, MAMA, MSMA, potassium arsenite and sodium arsenite; benzoylcyclohexanedione herbicides such as mesotrione, sulcotrione, tefuryltrione and tembotrione; benzofuranyl alkylsulfonate herbicides such as benfuresate and ethofumesate; carbamate herbicides such as asulam, carboxazole chlorprocarb, dichlormate, fenasulam, karbutilate and terbucarb; carbanilate herbicides such as barban, BCPC, carbasulam, carbetamide, CEPC, chlorbufam, chlorpropham, CPPC, desmedipham, phenisopham, phenmedipham, phenmedipham-ethyl, propham and swep; cyclohexene oxime herbicides such as alloxydim, butroxydim, clethodim, cloproxydim, cycloxydim, profoxydim, sethoxydim, tepraloxydim and tralkoxydim; cyclopropylisoxazole herbicides such as isoxachlortole and isoxaflutole; dicarboximide herbicides such as benzfendizone, cinidon-ethyl, flumezin, flumiclorac, flumioxazin and flumipropyn; dinitroaniline herbicides such as benfluralin, butralin, dinitramine, ethalfluralin, fluchloralin, isopropalin, methalpropalin, nitralin, oryzalin, pendimethalin, prodiamine, profluralin and trifluralin; dinitrophenol herbicides such as dinofenate, dinoprop, dinosam, dinoseb, dinoterb, DNOC, etinofen and medinoterb; diphenyl ether herbicides such as ethoxyfen; nitrophenyl ether herbicides such as acifluorfen, aclonifen, bifenox, chlomethoxyfen, chlornitrofen, etnipromid, fluorodifen, fluoroglycofen, fluoronitrofen, fomesafen, furyloxyfen, halosafen, lactofen, nitrofen, nitrofluorfen and oxyfluorfen; dithiocarbamate herbicides such as dazomet and metam; halogenated aliphatic herbicides such as alorac, chloropon, dalapon, flupropanate, hexachloroacetone, iodomethane, methyl bromide, monochloroacetic acid, SMA and TCA; imidazolinone herbicides such as imazamethabenz, imazamox, imazapic, imazapyr, imazaquin and imazethapyr; inorganic herbicides such as ammonium sulfamate, borax, calcium chlorate, copper sulfate, ferrous sulfate, potassium azide, potassium cyanate, sodium azide, sodium chlorate and sulfuric acid; nitrile herbicides such as bromobonil, bromoxynil, chloroxynil, dichlobenil, iodobonil, ioxynil and pyraclonil; organophosphorus herbicides such as amiprofos-methyl, anilofos, bensulide, bilanafos, butamifos, 2,4-DEP, DMPA, EBEP, fosamine, glufosinate, glyphosate and piperophos; phenoxy herbicides such as bromofenoxim, clomeprop, 2,4-DEB, 2,4-DEP, difenopenten, disul, erbon, etnipromid, fenteracol and trifopsime; phenoxyacetic herbicides such as 4-CPA, 2,4-D, 3,4-DA, MCPA, MCPA-thioethyl and 2,4,5-T; phenoxybutyric herbicides such as 4-CPB, 2,4-DB, 3,4-DB, MCPB and 2,4,5-TB; phenoxypropionic herbicides such as cloprop, 4-CPP, dichlorprop, dichlorprop-P, 3,4-DP, fenoprop, mecopropand mecoprop-P; aryloxyphenoxypropionic herbicides such as chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P and trifop; phenylenediamine herbicides such as dinitramine and prodiamine; pyrazolyl herbicides such as benzofenap, pyrazolynate, pyrasulfotole, pyrazoxyfen, pyroxasulfone and topramezone; pyrazolylphenyl herbicides such as fluazolate and pyraflufen; pyridazine herbicides such as credazine, pyridafol and pyridate; pyridazinone herbicides such as brompyrazon, chloridazon, dimidazon, flufenpyr, metflurazon, norflurazon, oxapyrazon and pydanon; pyridine herbicides such as aminopyralid, cliodinate, clopyralid, dithiopyr, fluoroxypyr, haloxydine, picloram, picolinafen, pyriclor, thiazopyr and triclopyr; pyrimidinediamine herbicides such as iprymidam and tioclorim; quaternary ammonium herbicides such as cyperquat, diethamquat, difenzoquat, diquat, morfamquat and paraquat; thiocarbamate herbicides such as butylate, cycloate, di-allate, EPTC, esprocarb, ethiolate, isopolinate, methiobencarb, molinate, orbencarb, pebulate, prosulfocarb, pyributicarb, sulfallate, thiobencarb, tiocarbazil, tri-allate and vernolate; thiocarbonate herbicides such as dimexano, EXD and proxan; thiourea herbicides such as methiuron; triazine herbicides such as dipropetryn, triaziflam and trihydroxytriazine; chlorotriazine herbicides such as atrazine, chlorazine, cyanazine, cyprazine, eglinazine, ipazine, mesoprazine, procyazine, proglinazine, propazine, sebuthylazine, simazine, terbuthylazine and trietazine; methoxytriazine herbicides such as atraton, methometon, prometon, secbumeton, simeton and terbumeton; methylthiotriazine herbicides such as ametryn, aziprotryne, cyanatryn, desmetryn, dimethametryn, methoprotryne, prometryn, simetryn and terbutryn; triazinone herbicides such as ametridione, amibuzin, hexazinone, isomethiozin, metamitron and metribuzin; triazole herbicides such as amitrole, cafenstrole, epronaz and flupoxam; triazolone herbicides such as amicarbazone, bencarbazone, carfentrazone, flucarbazone, propoxycarbazone, sulfentrazone and thiencarbazone-methyl; triazolopyrimidine herbicides such as cloransulam, diclosulam, florasulam, flumetsulam, metosulam, penoxsulam and pyroxsulam; uracil herbicides such as butafenacil, bromacil, flupropacil, isocil, lenacil and terbacil; 3-phenyluracils; urea herbicides such as benzthiazuron, cumyluron, cycluron, dichloralurea, diflufenzopyr, isonoruron, isouron, methabenzthiazuron, monisouron and noruron; phenylurea herbicides such as anisuron, buturon, chlorbromuron, chloreturon, chlorotoluron, chloroxuron, daimuron, difenoxuron, dimefuron, diuron, fenuron, fluometuron, fluothiuron, isoproturon, linuron, methiuron, methyldymron, metobenzuron, metobromuron, metoxuron, monolinuron, monuron, neburon, parafluoron, phenobenzuron, siduron, tetrafluoron and thidiazuron; pyrimidinylsulfonylurea herbicides such as amidosulfuron, azimsulfuron, bensulfuron, chlorimuron, cyclosulfamuron, ethoxysulfuron, flazasulfuron, flucetosulfuron, flupyrsulfuron, foramsulfuron, halosulfuron, imazosulfuron, mesosulfuron, nicosulfuron, orthosulfamuron, oxasulfuron, primisulfuron, pyrazosulfuron, rimsulfuron, sulfometuron, sulfosulfuron and trifloxysulfuron; triazinylsulfonylurea herbicides such as chlorsulfuron, cinosulfuron, ethametsulfuron, iodosulfuron, metsulfuron, prosulfuron, thifensulfuron, triasulfuron, tribenuron, triflusulfuron and tritosulfuron; thiadiazolylurea herbicides such as buthiuron, ethidimuron, tebuthiuron, thiazafluoron and thidiazuron; and unclassified herbicides such as acrolein, allyl alcohol, azafenidin, benazolin, bentazone, benzobicyclon, buthidazole, calcium cyanamide, cambendichlor, chlorfenac, chlorfenprop, chlorflurazole, chlorflurenol, cinmethylin, clomazone, CPMF, cresol, ortho-dichlorobenzene, dimepiperate, endothal, fluoromidine, fluridone, fluorochloridone, flurtamone, fluthiacet, indanofan, methazole, methyl isothiocyanate, nipyraclofen, OCH, oxadiargyl, oxadiazon, oxaziclomefone, pentachlorophenol, pentoxazone, phenylmercury acetate, pinoxaden, prosulfalin, pyribenzoxim, pyriftalid, quinoclamine, rhodethanil, sulglycapin, thidiazimin, tridiphane, trimeturon, tripropindan and tritac.

The herbicidal compounds of the present invention can, further, be used in conjunction with glyphosate, glufosinate, dicamba, imidazolinones or 2,4-D on glyphosate-tolerant, glufosinate-tolerant, dicamba-tolerant, imidazolinone-tolerant or 2,4-D-tolerant crops. It is generally preferred to use the compounds of the invention in combination with herbicides that are selective for the crop being treated and which complement the spectrum of weeds controlled by these compounds at the application rate employed. It is further generally preferred to apply the compounds of the invention and other complementary herbicides at the same time, either as a combination formulation or as a tank mix.

The compounds of the present invention can generally be employed in combination with known herbicide safeners, such as benoxacor, benthiocarb, brassinolide, cloquintocet (mexyl), cyometrinil, daimuron, dichlormid, dicyclonon, dimepiperate, disulfoton, fenchlorazole-ethyl, fenclorim, flurazole, fluxofenim, furilazole, isoxadifen-ethyl, mefenpyrdiethyl, MG 191, MON 4660, naphthalic anhydride (NA), oxabetrinil, R29148 and N-phenyl-sulfonylbenzoic acid amides, to enhance their selectivity. They can additionally be employed to control undesirable vegetation in many crops that have been made tolerant to or resistant to them or to other herbicides by genetic manipulation or by mutation and selection. For example, corn, wheat, rice, soybean, sugarbeet, cotton, canola, and other crops that have been made tolerant or resistant to compounds that are acetolactate synthase inhibitors in sensitive plants can be treated. Many glyphosate and glufosinate tolerant crops can be treated as well, alone or in combination with these herbicides. Some crops (e.g. cotton) have been made tolerant to auxinic herbicides such as 2,4-dichlorophenoxyacetic acid. These herbicides may be used to treat such resistant crops or other auxin tolerant crops.

While it is possible to utilize the 2-(substituted phenyl)-6-amino-5-alkoxy, thioalkoxy and aminoalkyl-4-pyrimidinecarboxylate compounds of Formula I directly as herbicides, it is preferable to use them in mixtures containing an herbicidally effective amount of the compound along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with the compounds of Formula I or other composition ingredients. Such mixtures can be designed for application directly to weeds or their locus or can be concentrates or formulations that are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methanol, ethanol, isopropanol, amyl alcohol, ethylene glycol, propylene glycol, glycerine, N-methyl-2-pyrrolidinone, N,N-dimethyl alkylamides, dimethyl sulfoxide, liquid fertilizers and the like. Water is generally the carrier of choice for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, and the like.

It is usually desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Typical surface-active agents include salts of alkyl sulfates, such as diethanol-ammonium lauryl sulfate; alkylarylsulfonate salts, such as calcium dodecyl-benzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alky-lnaphthalene-sulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethyl-ammonium chloride; polyethylene glycol esters of fatty acids, such as poly-ethylene glycol stearate; block copolymers of ethylene oxide and propylene oxide; and salts of mono and dialkyl phosphate esters.

Other adjuvants commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of the active ingredients in the herbicidal compositions of this invention is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as water, before application. The diluted compositions usually applied to weeds or the locus of weeds generally contain about 0.0001 to about 1 weight percent active ingredient and preferably contain about 0.001 to about 0.05 weight percent.

The present compositions can be applied to weeds or their locus by the use of conventional ground or aerial dusters, sprayers, and granule applicators, by addition to irrigation water, and by other conventional means known to those skilled in the art.

The following Examples are presented to illustrate the various aspects of this invention and should not be construed as limitations to the claims.

EXAMPLES

1. Preparation of 4-Chloro-2,5-difluorophenylamine

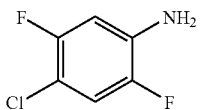

Tin (II) chloride dihydrate (15.5 g, 68.7 mmol) was dissolved in ethyl acetate (50 mL) and 1-chloro-2,5-difluoro-4-nitrobenzene (2.65 g, 13.7 mmol) was added dropwise. The reaction mixture was then stirred at 70° C. for 1 h. The reaction mixture was then carefully added to saturated aqueous sodium bicarbonate and then extracted with ethyl acetate. The organic phase was washed several more times with water, dried, filtered, concentrated and purified by flash chromatography on silica gel (hexane/diethyl ether) to give the title compound as a white solid (1.65 g, 73.9% yield): $^1$H NMR (CDCl$_3$): δ 7.02 (dd, 1H), 6.57 (dd, 1H), 3.81 (br s, 2H).

2. Preparation of 1-Bromo-4-chloro-2,5-difluorobenzene

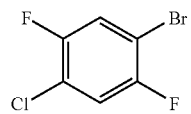

Anhydrous copper (II) bromide (2.7 g, 12.1 mmol) and t-butyl nitrite (1.56 g, 15.1 mmol) were combined in anhydrous acetonitrile (25 mL). The resulting mixture was heated to 65° C. and a solution of 4-chloro-2,5-difluoro-phenylamine (1.65 g, 10.1 mmol) in anhydrous acetonitrile (2 mL) was added dropwise (vigorous gas evolution was noted). After the reaction mixture cooled ambient temperature, it was added to 2N HCl and extracted with ether twice. The organic extracts were then combined, washed with 2N HCl, washed with saturated sodium bicarbonate, dried, concentrated and purified by flash chromatography on silica gel (hexanes) to give the title compound as a white solid (1.11 g, 48.4% yield): $^1$H NMR (CDCl$_3$): δ 7.38 (dd, 2H), 7.21 (dd, 2H).

3. Preparation of 2-(4-Chloro-2,5-difluorophenyl)-4,4,5,5-tetramethyl-[1,3,2]dioxaborolane

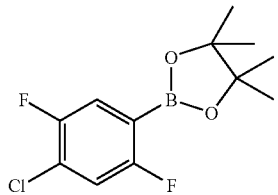 [SMILES: CC1(C)OB(c2cc(F)c(Cl)cc2F)OC1(C)C]

1-Bromo-4-chloro-2,5-difluorobenzene (1.11 g, 4.9 mmol) was dissolved in tetrahydrofuran (THF; 15 mL) and cooled to −10° C. A 2.0M solution of isopropyl-magnesium chloride (2.7 mL, 5.4 mmol) in THF was added dropwise via a syringe. The reaction mixture was stirred at −10° C. for 1 hour, allowed to warm toward 0° C. for 1 hour, then cooled to −10° C. again. A solution of 2-isopropoxy-4,4,5,5-tetramethyl-1,3,2-dioxaborolane (1.0 g, 5.4 mmol) in THF (1.0 mL) was then added dropwise and the reaction was allowed to warm to ambient temperature. The reaction mixture was then added to diethyl ether and extracted with 1N sodium hydroxide twice. The aqueous phases were combined, acidified to pH 3 with concentrated HCl, and extracted with dichloromethane twice. The organic phases were combined, dried, filtered and concentrated to give the title compound (0.97 g, 72.3% yield) that was used without further purification: $^1$H NMR (CDCl$_3$): δ 7.45 (dd, 1H), 7.09 dd, 1H), 1.36 (s, 12H).

Another compound prepared by the procedure of Example 3 is:

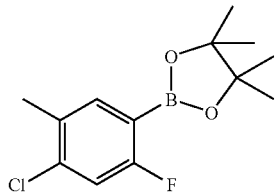

2-(4-Chloro-2-fluoro-5-methylphenyl)-4,4,5,5-tetramethyl-[1,3,2]dioxaborolane: $^1$H NMR (CDCl$_3$): δ 7.58 (d, 1H), 7.03 (d, 1H), 2.32 (s, 3H), 1.35 (s, 12H).

4. Preparation of 1-(5-Bromo-2-chlorophenyl)-ethanol

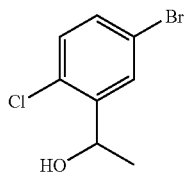

Sodium borohydride (1.182 g, 51.4 mmol) was added to a stirred solution of 1-(5-bromo-2-chlorophenyl)ethanone (10 g, 42.8 mmol) in methanol at 0° C., The resulting bubbling white mixture was allowed to warm to room temperature and stirred for 2 h. The reaction mixture was quenched with acetone (50 mL) and concentrated by rotary evaporation. The residue was partitioned between ethyl acetate and water. The organic phase was dried and concentrated to yield the title compound (10 g, 42.5 mmol, 99% yield) as a white solid: $^1$H NMR (CDCl$_3$): δ 7.75 (d, 1H), 7.32 (m, 1H), 7.19 (m, 1H), 5.23 (q, 1H), 1.95 (d, 1H), 1.48 (d, 3H).

Another compound prepared by the procedure of Example 4 is:

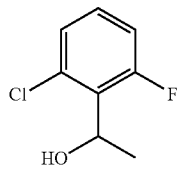

1-(2-Chloro-6-fluorophenyl)ethanol: $^1$H NMR (300 MHz, CDCl$_3$) δ 7.14-7.22 (m, 2H), 6.99 (m, 1H), 5.38 (m, 1H), 2.48 (m, 1H), 1.63 (dd, 3H, J=1, 7 Hz).

5. Preparation of 4-Bromo-1-chloro-2-(1-fluoro-ethyl)-benzene

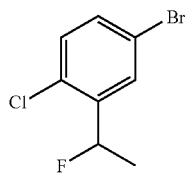

Bis(2-methoxyethyl)aminosulfur trifluoride (4.5 g, 20.34 mmol) was added to a stirred solution of 1-(5-bromo-2-chlorophenyl)ethanol (3.99 g, 16.95 mmol) in dichloromethane (50 mL) at 0° C. The resulting solution was stirred at 0° C. for 3 h. The reaction mixture was quenched with a 5% solution of aqueous sodium bicarbonate (100 mL) and the resulting bubbling biphasic reaction mixture was vigorously stirred at 0° C. for 15 m. The reaction mixture was diluted with water (50 mL) and extracted with dichloromethane twice. The combined organic layers were washed with 1M hydrochloric acid, dried and concentrated by rotary evaporation. The product was purified by flash chromatography on silica gel (hexanes) to yield the title compound (2.65 g, 11.16 mmol, 65.8% yield) as a clear oil: $^1$H NMR (CDCl$_3$): δ 7.65 (d, 1H), 7.37 (m, 1H), 7.20 (m, 1H), 5.88 (dq, 1H), 1.61 (dd, 3H).

Another compound prepared by the procedure of Example 5 is:

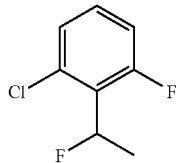

1-Chloro-3-fluoro-2-(1-fluoroethyl)benzene: $^1$H NMR (300 MHz, CDCl$_3$) δ 7.15-7.26 (m, 2H), 7.02 (m, 1H), 6.12 (dq, 1H, J=6, 46 Hz), 1.76 (ddd, 3H, J=1, 7, 23 Hz).

6. Preparation of 2-[4-Chloro-3-(1-fluoro-ethyl)-phenyl]-4,4,5,5-tetramethyl-[1,3,2]dioxaborolane

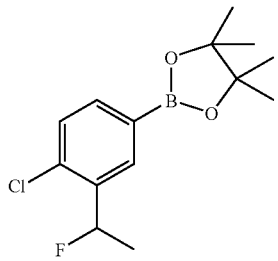 [SMILES: CC(F)c1cc(B2OC(C)(C)C(C)(C)O2)ccc1Cl]

4-Bromo-1-chloro-2-(1-fluoroethyl)benzene (2.55 g, 10.74 mmol) was dissolved in dry diethyl ether (50 mL) and cooled to −75° C. n-Butyllithium (4.72 mL, 11.81 mmol) was added dropwise keeping the temperature below −70° C. The reaction mixture was then stirred for 15 min, then 2-isopropoxy-4,4,5,5-tetramethyl-1,3,2-dioxaborolane (2.197 g, 11.81 mmol) was added and the reaction mixture was allowed to warm to room temperature. The reaction mixture was then diluted with water and diethyl ether. The aqueous phase was acidified with 12N HCl and the product was then extracted with diethyl ether. The organic phase was dried and concentrated under vacuum to yield the title compound (1.55 g, 5.45 mmol, 50.7% yield) as a white solid: $^1$H NMR (CDCl$_3$): δ 7.94 (d, 1H), 7.65 (m, 1H), 7.36 (m, 1H), 5.96 (dq, 1H), 1.64 (dd, 3H), 1.34 (s, 12H).

Another compound prepared by the procedure of Example 6 is:

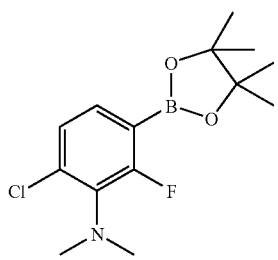 [SMILES: CN(C)c1c(Cl)ccc(B2OC(C)(C)C(C)(C)O2)c1F]

[6-Chloro-2-fluoro-3-(4,4,5,5-tetramethyl-[1,3,2]dioxaborolan-2-yl) phenyl]-dimethylamine: $^1$H NMR (CDCl$_3$): δ 7.35 (m, 1H), 7.13 (m, 1H), 2.85 (d, 6H), 1.36 (s, 12H).

7. Preparation of 2-(4-Chloro-2,3-difluorophenyl)-4,4,5,5-tetramethyl-[1,3,2]dioxaborolane

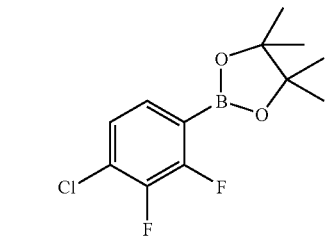 [SMILES: CC1(C)OB(c2ccc(Cl)c(F)c2F)OC1(C)C]

A 2.5 M solution of n-butyllithium (2.69 ml, 6.73 mmol) in hexanes was added dropwise to a solution of 1-chloro-2,3-difluorobenzene (1 g, 6.73 mmol) in THF (25 mL) cooled to −78° C. After 45 min at −78° C., 2-isopropoxy-4,4,5,5-tetramethyl-1,3,2-dioxaborolane (1.253 g, 6.73 mmol) was added dropwise after which the reaction mixture was allowed to warm to ambient temperature. The reaction mixture was diluted with water and ethyl acetate; and the organic phase was extracted twice with water. The aqueous extracts were combined and acidified with 12N HCl to pH 3. The product was then extracted with ethyl acetate. The organic phase was dried and concentrated under vacuum to yield the title compound as an oil product (0.93 g, 50% yield): $^1$H NMR (CDCl$_3$): δ 7.42 (m, 1H), 7.17 (m, 1H), 1.37 (s, 12H).

8. Preparation of 2-(4-Chloro-2-fluoro-3-(1-fluoroethyl)phenyl)-4,4,5,5-tetramethyl-1,3,2-dioxaborolane

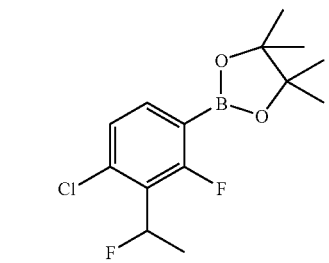 [SMILES: CC(F)c1c(Cl)ccc(B2OC(C)(C)C(C)(C)O2)c1F]

A 2.5 M solution of n-butyllithium (13 mL, 33 mmol) was added to a stirred solution of diisopropylamine (5.0 mL, 35 mmol) in tetrahydrofuran THF (50 mL) at −78° C. The resulting colorless solution was stirred at −78° C. for 20 m, warmed to 0° C. for 20 m, and then cooled back to −78° C. for 20 m. A solution of 1-chloro-3-fluoro-2-(1-fluoroethyl)benzene (4.8 g, 27 mmol, 1.0 equiv) in THF (20 mL) at −78° C. was transferred to the base solution via cannula. The resulting dark brown solution was stirred at −78° C. for 2 h. 2-Isopropoxy-4,4,5,5-tetramethyl-1,3,2-dioxaborolane (8.3 mL, 41 mmol, 1.5 equiv) was added and the brown solution was slowly warmed to 23° C. over 20 h. The reaction mixture was diluted with 0.1M hydrochloric acid (300 mL) and extracted with dichloromethane three times. The combined organic layers were dried, filtered and concentrated by rotary evaporation to afford the title compound as a brown oil that solidified into a semi-solid upon standing (7.7 g, 94% yield). $^1$H NMR (300 MHz, CDCl$_3$) δ 7.62 (m, 1H), 7.17 (m, 1H), 6.13 (dq, 1H, J=6, 46 Hz), 1.75 (ddd, 3H, J=1, 7, 23 Hz), 1.36 (s, 12H).

9. Preparation of 6-Amino-2-chloro-5-methoxypyrimidine-4-carboxylic acid methyl ester

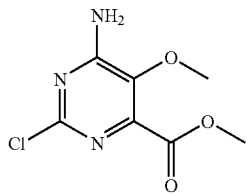

2,6-Dichloro-5-methoxypyrimidine-4-carboxylic acid methyl ester (750 mg, 3.16 mmol; see *J. Med. Chem.* 49(5), 1693-1705; 2006 for preparation) was dissolved in chloroform and 2N ammonia in methanol (2 eq) was added dropwise while in a cooling bath. The reaction mixture was stirred for 30 min, after which an additional 2 eq of 2N ammonia in methanol was added. The reaction was stirred at ambient temperature for 16 h. Additional 2N ammonia in methanol (2 eq) was added. The reaction was stirred for 2 h during which time a solid precipitated. The solid was filtered off and water was added to the filtrate. The crude material was extracted from the filtrate with dichloromethane three times and the combined organic phases were washed with brine, dried and concentrated under vacuum. The product was purified by flash chromatography on silica gel (hexane/ethyl acetate gradient) to provide the title compound (202 mg, 29% yield): mp 162-167° C.; $^1$H NMR (CDCl$_3$): δ 5.75 (br s, 2H), 3.97 (s, 3H), 3.92 (s, 3H).

10. Preparation of 2,6-Dichloro-5-methoxy-pyrimidin-4-ylamine

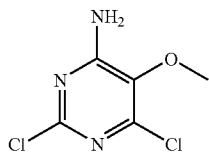

2,4,6-Trichloro-5-methoxypyrimidine (1.0 g, 4.7 mmol, see U.S. Pat. No. 3,984,411 for preparation) was dissolved in 15 mL dry dimethyl sulfoxide (DMSO) and treated with a stream of ammonia gas for 30 min. The mixture was poured into 30 mL water and the precipitated product was collected by filtration and washed with water. This solid was dissolved in 40 mL ethyl acetate, washed twice with water, washed once with brine, dried and evaporated to give the title compound (800 mg, 88% yield): mp 155-156° C.: $^1$H NMR (DMSO-d$_6$+D$_2$O) δ 3.71 (s, 3H).

11. Preparation of 6-Amino-2-chloro-5-methoxypyrimidine-4-carboxylic acid ethyl ester

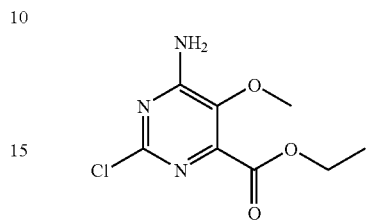

2,6-Dichloro-5-methoxypyrimidin-4-ylamine (5.0 g, 26 mmol) was combined in 75 mL absolute ethanol with sodium acetate (2.1 g, 26 mmol), palladium acetate (280 mg, 0.91 mmol) and DPPB (1.1 g, 2.6 mmol) in a 300 mL stirred pressure reactor. The reactor was purged and pressurized to 300 psi with carbon monoxide, and heated at 110° C. for 7 h. The volatiles were removed under vacuum and the residue was taken up in ethyl acetate and water. The aqueous phase was extracted with an additional ethyl acetate; and the combined extracts were washed with brine, dried and evaporated. The residue was purified by flash chromatography on silica gel (0-30% ethyl acetate gradient in hexanes) to give the title compound (1.4 g, 23% yield): mp 118-119° C. $^1$H NMR (CDCl$_3$) δ 6.18 (br s, 2H), 4.45 (q, 2H), 3.91 (s, 3H), 1.42 (t, 3H).

12. Preparation of 6-amino-2-(4-chloro-2-fluoro-3-methoxyphenyl)-5-methoxypyrimidine-4-carboxylic acid methyl ester (Compound 1)

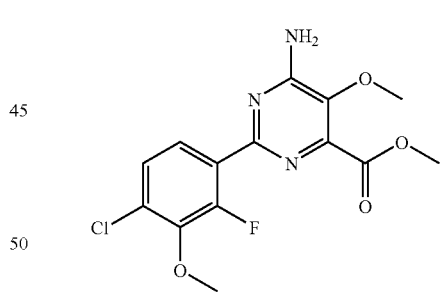

6-Amino-2-chloro-5-methoxypyrimidine-4-carboxylic acid methyl ester (0.2 g, 0.9 mmol), 4-chloro-2-fluoro-3-methoxyphenylboronic acid (0.29 g, 1.4 mmol), bis(triphenylphosphine)palladium(II) dichloride (65 mg, 0.1 mmol), and cesium fluoride (0.28 g, 1.9 mmol) were combined in 1 mL of 1,2-dimethoxyethane and 1 mL of water. The reaction mixture was heated in a CEM microwave at 100° C. for 15 min (other temperature/time pairs used in the subsequent examples were 110° C. for 15 min and 150° C. for 5 min) The cooled reaction mixture was diluted with ethyl acetate, washed with water, washed with brine, dried and concentrated. The product was purified by flash chromatography on silica gel (hexane/ethyl acetate gradient) to yield the title compound (162 mg, 51.1% yield): mp 155-158° C.; $^1$H NMR (CDCl₃): δ 7.58 (dd, 1H), 7.20 (dd, 1H), 5.56 (br s, 2H) 4.00 (s, 3H), 3.99 (d, 3H), 3.94 (s, 3H).

Other compounds prepared by the procedure of Example 12 are:

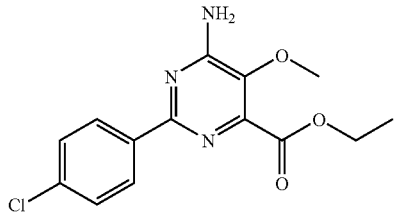 [SMILES: CCOC(=O)c1nc(-c2ccc(Cl)cc2)nc(N)c1OC]

6-Amino-2-(4-chlorophenyl)-5-methoxypyrimidine-4-carboxylic acid ethyl ester (Compound 2): ¹H NMR (CDCl₃): δ 8.25 (d, 2H), 7.39 (d, 2H), 5.32 (br s, 2H), 4.48 (q, 2H), 3.92 (s, 3H), 1.42 (t, 3H).

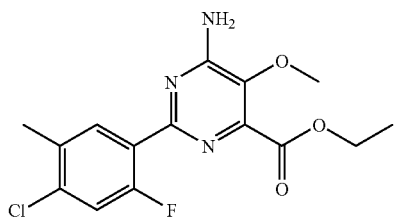 [SMILES: CCOC(=O)c1nc(-c2cc(C)c(Cl)cc2F)nc(N)c1OC]

6-Amino-2-(4-chloro-2-fluoro-5-methylphenyl)-5-methoxypyrimidine-4-carboxylic acid ethyl ester (Compound 3): ¹H NMR (CDCl₃): δ 7.82 (d, 2H), 7.18 (d, 2h), 5.38 (br s, 2H), 4.45 (q, 2H), 3.93 (s, 3H), 2.38 (s, 3H), 1.42 (t, 3H).

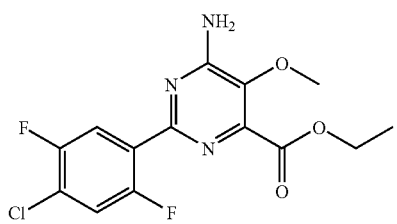

6-Amino-2-(4-chloro-2,5-difluorophenyl)-5-methoxypyrimidine-4-carboxylic acid ethyl ester (Compound 4): ¹H NMR (CDCl₃): δ 7.81 (dd, 1H), 7.21 (dd, 1H), 5.41 (br s, 2H), 4.47 (q, 2H), 3.94 (s, 3H). 1.42 (t, 3H).

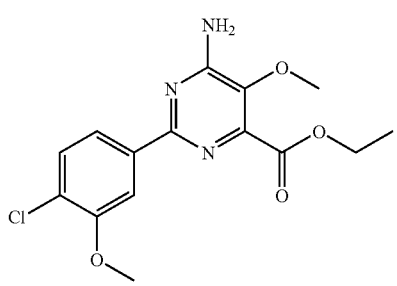 [SMILES: CCOC(=O)c1nc(-c2ccc(Cl)c(OC)c2)nc(N)c1OC]

6-Amino-2-(4-chloro-3-methoxyphenyl)-5-methoxypyrimidine-4-carboxylic acid ethyl ester (Compound 5): ¹H NMR (CDCl₃): δ 7.9 (m, 2H), 7.4 (d, 1H), 5.32 (br s, 2H), 4.49 (q, 2H), 4.01( )s, 3H), 3.92 (s, 3H), 1.42 (q, 3H).

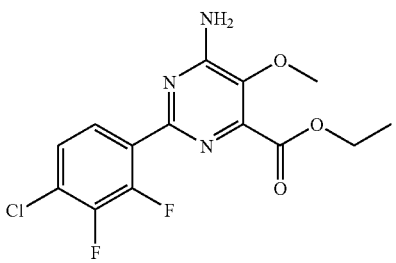 [SMILES: CCOC(=O)c1nc(-c2ccc(Cl)c(F)c2F)nc(N)c1OC]

6-Amino-2-(4-chloro-2,3-difluorophenyl)-5-methoxypyrimidine-4-carboxylic acid ethyl ester (Compound 6): ¹H NMR (CDCl₃): δ 7.7 (m, 1H), 7.2 (m, 1H), 5.38 (br s, 2H), 4.47 (q, 2H), 3.94 (s, 3H), 1.44 (t, 3H).

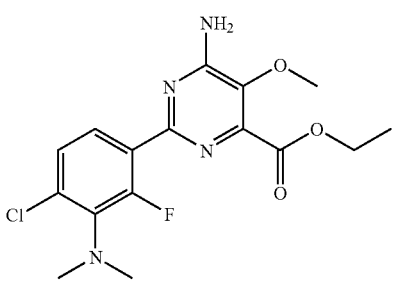 [SMILES: CCOC(=O)c1nc(-c2ccc(Cl)c(N(C)C)c2F)nc(N)c1OC]

6-Amino-2-(4-chloro-3-dimethylamino-2-fluorophenyl)-5-methoxypyrimidine-4-carboxylic acid ethyl ester (Compound 7): ¹H NMR (CDCl₃): δ 7.54 (m, 1H), 7.17 (m, 1H), 5.36 (br s, 2H), 4.46 (q, 2H), 3.93 (s, 3H), 2.89 (d, 6H), 1.44 (q, 3H).

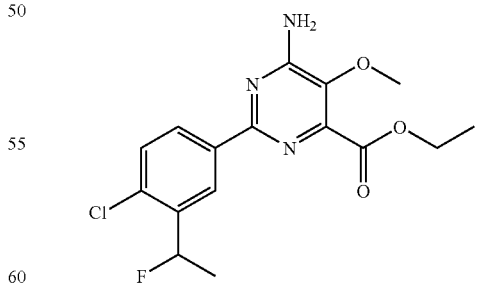

6-Amino-2-[4-chloro-3-(1-fluoroethyl)phenyl]-5-methoxypyrimidine-4-carboxylic acid ethyl ester (Compound 8): ¹H NMR (CDCl₃): δ 8.47 (d, 1H), 8.22 (m, 1H), 7.37 (m, 1H), 5.98 (dq, 1H), 5.31 (br s, 2H), 4.48 (q, 2H), 3.91 (s, 3H), 1.68 (dd, 3H), 1.46 (t, 3H).

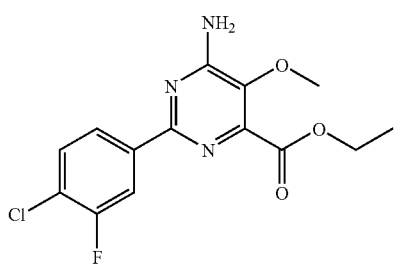 [SMILES: CCOC(=O)c1nc(-c2ccc(Cl)c(F)c2)nc(N)c1OC]

6-Amino-2-(4-chloro-3-fluorophenyl)-5-methoxypyrimidine-4-carboxylic acid ethyl ester (Compound 9): $^1$H NMR (CDCl$_3$) δ 1.45 (t, J=7.25 Hz, 3H) 3.91 (s, 3H), 4.48 (q, J=7.25 Hz, 2H), 5.35 (bs, 2H) 7.42 (t, J=8.24 Hz, 1H) 8.05-8.14 (m, 1H).

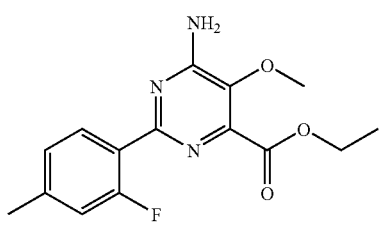 [SMILES: CCOC(=O)c1nc(-c2ccc(C)cc2F)nc(N)c1OC]

6-Amino-2-(2-fluoro-4-methylphenyl)-5-methoxypyrimidine-4-carboxylic acid ethyl ester (Compound 10): $^1$H NMR (CDCl$_3$) δ 1.43 (t, J=7.07 Hz, 3H) 2.37 (s, 3H) 3.92 (s, 3H), 4.47 (q, J=7.08 Hz, 2H), 5.41 (bs, 2H) 6.98 (d, J=8.08 Hz, 1H) 7.62 (d, J=8.08 Hz, 1H).

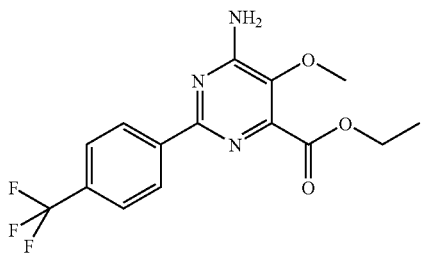 [SMILES: CCOC(=O)c1nc(-c2ccc(C(F)(F)F)cc2)nc(N)c1OC]

6-Amino-5-methoxy-2-(4-trifluoromethylphenyl)pyrimidine-4-carboxylic acid ethyl ester (Compound 11): $^1$H NMR (CDCl$_3$) δ 1.46 (t, J=7.07 Hz, 3H) 3.93 (s, 3H), 4.50 (q, J=7.07 Hz, 2H), 5.37 (bs, 2H) 7.67 (d, J=8.24 Hz, 1H) 8.43 (d, J=8.08 Hz, 1H).

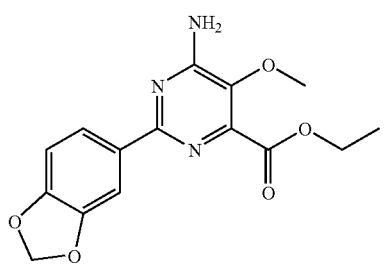 [SMILES: CCOC(=O)c1nc(-c2ccc3c(c2)OCO3)nc(N)c1OC]

6-Amino-2-benzo[1,3]dioxol-5-yl-5-methoxypyrimidine-4-carboxylic acid ethyl ester (Compound 12): $^1$H NMR (CDCl$_3$) δ 1.44 (t, J=6.93 Hz, 3H) 3.69 (s, 3H), 4.47 (q, J=7.25 Hz, 2H), 5.27 (bs, 2H) 6.00 (s, 3H) 6.85 (d, 1H, J=8.24 Hz) 7.80 (d, J=1.65 Hz, 1H) 7.90 (dd, J=1.65, 1H).

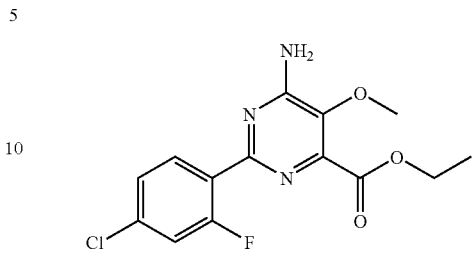

6-Amino-2-(4-chloro-2-fluorophenyl)-5-methoxypyrimidine-4-carboxylic acid ethyl ester (Compound 13): $^1$H NMR (CDCl$_3$) δ 7.92 (t, 1H, J=8 Hz), 7.14-7.22 (m, 2H), 5.39 (br s, 2H), 4.48 (q, 2H, J=7 Hz), 3.94 (s, 3H), 1.44 (t, 3H, J=7 Hz).

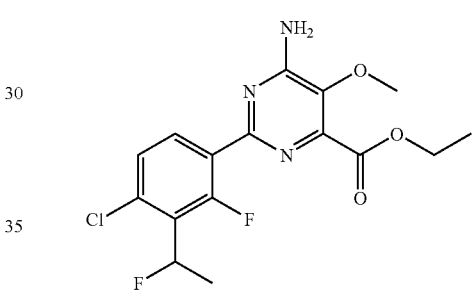

6-Amino-2-[4-chloro-2-fluoro-3-(1-fluoroethyl)phenyl]-5-methoxypyrimidine-4-carboxylic acid ethyl ester (Compound 14): $^1$H NMR (CDCl$_3$) δ 7.84 (t, 1H, J=8 Hz), 7.24 (m, 1H), 6.17 (dq, 1H, J=7, 118 Hz), 5.43 (br s, 2H), 4.48 (q, 2H, J=7 Hz), 3.94 (s, 3H), 1.78 (ddd, 3H, J=1, 7, 23 Hz), 1.44 (t, 3H, J=7 Hz).

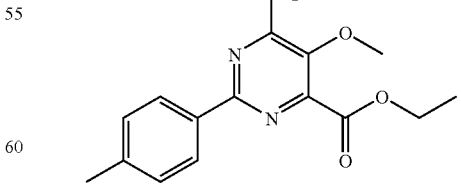

6-Amino-5-methoxy-2-p-tolylpyrimidine-4-carboxylic acid ethyl ester (Compound 15): $^1$H NMR (CDCl$_3$) δ 8.20 (d, 2H, J=8 Hz), 7.23 (d, 2H, J=8 Hz), 5.27 (br s, 2H), 4.48 (q, 2H, J=7 Hz), 3.90 (s, 3H), 2.39 (s, 3H), 1.46 (t, 3H, J=7 Hz).

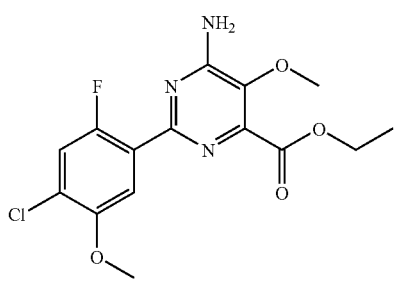 [SMILES: CCOC(=O)c1nc(-c2cc(OC)c(Cl)cc2F)nc(N)c1OC]

6-Amino-2-(4-chloro-2-fluoro-5-methoxyphenyl)-5-methoxypyrimidine-4-carboxylic acid ethyl ester (Compound 16): $^1$H NMR (CDCl$_3$) δ 7.52 (d, 1H, J=7 Hz), 7.20 (d, 1H, J=10 Hz), 5.40 (br s, 2H), 4.48 (q, 2H, J=7 Hz), 3.95 (s, 3H), 3.94 (s, 3H), 1.44 (t, 3H, J=7 Hz).

13. Preparation of 4-Chloro-2-fluoro-3-methoxybenzaldehyde

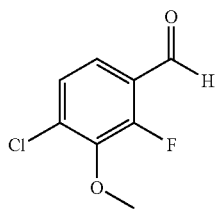

1-Bromo-4-chloro-2-fluoro-3-methoxybenzene (23.7 g, 99 mmol, see U.S. Pat. No. 7,300,907 for preparation) was dissolved in dry diethyl ether and cooled to −78° C. 2.5M n-Butyllithium in hexanes (44 mL, 110 mmol) was added in portions, keeping the temperature below −70° C. during the addition. DMF (15.5 mL, 200 mmol) was then added in portions, keeping the temperature below −60° C. The reaction mixture was then allowed to warm to ambient temperature and quenched with water. The organic phase was dried and concentrated. The product was purified by flash chromatography on silica gel (hexane/ethyl acetate gradient) to yield the title compound in sufficient purity for subsequent reactions (11.4 g, 61% yield): $^1$H NMR (CDCl$_3$) δ 10.32 (s, 1H), 7.55 (m, 1H), 7.3 (m, 1H), 4.05 (d, 3H).

14. Preparation of 4-Chloro-2-fluoro-3-methoxybenzonitrile

4-chloro-2-fluoro-3-methoxybenzaldehyde (30 g, 0.16 mole) was combined with hydroxylamine hydrochloride (13 g, 0.19 mole) in 250 mL ethanol, treated with pyridine (16 mL) and heated to reflux for 1 h. After cooling and removal of volatiles under vacuum, the residue was taken up in 300 mL ethyl acetate plus 100 mL water. The organic phase was washed with water, washed with brine, dried and evaporated to give 31 g of the crude oxime. The oxime was dissolved in 250 mL acetonitrile, treated with cupric acetate monohydrate (3.0 g, 15 mmol) and heated to reflux for 3 h. Upon cooling, the volatiles were removed by evaporation and the residue was taken up in ethyl acetate. This solution was washed twice with 1M H$_2$SO$_4$, washed once with brine, dried and evaporated to give 28 g of the title compound (28 g, 94% yield): mp 94-97° C.: $^1$H NMR (CDCl$_3$) δ 7.27 (m, 2H), 4.03 (d, 3H).

15. Preparation of 4-Chloro-2-fluoro-3-methoxybenzamidine hydrochloride

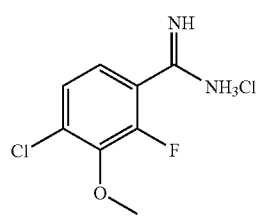

4-chloro-2-fluoro-3-methoxybenzonitrile (3.0 g, 16 mmol) was dissolved in 7 mL dry THF and added dropwise to a 1M solution of lithium bis(trimethylsilyl)amide (18 mL, 18 mmol). After stirring at 25° C. for 5 h, the mixture was treated with 25 mL of 2-propanol saturated with gaseous HCl. Upon standing at 5° C. for 18 h, the mixture was diluted with 30 mL ether whereupon the product precipitated. The precipitated product was collected by filtration, washed with ether and dried under vacuum to give the title compound (3.0 g, 78.6% yield): $^1$H NMR (DMSO-d$_6$) δ 9.70 (br d, 3H), 7.58 (m, 1H), 7.46 (m, 1H), 7.39 (br d, 1H), 3.96 (s, 3H).

16. Preparation of 4,6-Dichloro-2-(4-chloro-2-fluoro-3-methoxyphenyl)-5-methoxypyrimidine

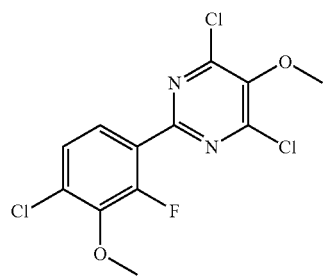 [SMILES: COc1c(Cl)nc(-c2ccc(Cl)c(OC)c2F)nc1Cl]

Sodium methoxide was prepared by dissolution of sodium (720 mg, 31 mmol) in 20 mL dry methanol. 4-Chloro-2-fluoro-3-methoxybenzamidine hydrochloride (2.5 g, 11 mmol) and dimethyl methoxymalonate (1.5 mL, 1.8 g, 11 mmol) were added to the cooled solution, heated at 45° C. for 2.5 h and then stirred at 25° C. for 18 h. The volatiles were removed under vacuum and the residue was taken up in 50 mL of water and washed with ether. The pH of the aqueous phase was adjusted to 3 with 1M HCl. The precipitated product was collected by filtration, washed with water, and dried under vacuum at 80° C. to give 2.1 g of the intermediate 2-(4-chloro-2-fluoro-3-methoxyphenyl)-5-methoxy-pyrimidine-4,6- diol. This material was treated with POCl$_3$ (4.0 mL, 6.4 g, 42 mmol) plus N,N-dimethylaniline (1.0 mL, 940 mg, 7.8 mmol) and heated to 85° C. for 90 min. After cooling, excess POCl$_3$ was removed under vacuum and the residue was taken up in 20 mL ice-water and 50 mL ethyl acetate. The organic phase was washed with water, washed with brine, dried and evaporated to give the title compound (2.0 g, 54% yield over two steps): mp 137-138° C.: $^1$H NMR (CDCl$_3$) δ 7.74 (dd, 1H), 7.24 (dd, 1H), 4.02 (s, 3H), 4.02 (s, 3H).

Another compound prepared by the procedures of Example 16 is:

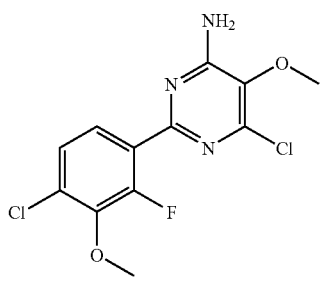 [SMILES: COc1c(N)nc(-c2ccc(Cl)c(OC)c2F)nc1Cl]

[4,6-Dichloro-2-(4-chloro-2-fluoro-3-methoxyphenyl)pyrimidin-5-yl]-dimethyl-amine: $^1$H NMR (CDCl$_3$) δ 7.73 (dd, 1H), 7.22 (dd, 1H), 4.02 (s, 3H), 2.93 (s, 6H).

17. Preparation of 6-Chloro-2-(4-chloro-2-fluoro-3-methoxyphenyl)-5-methoxypyrimidin-4-ylamine

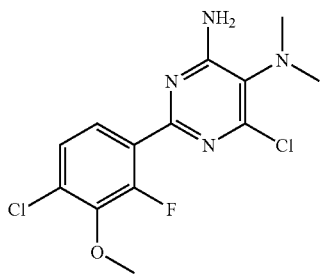 [SMILES: COc1c(Cl)ccc(-c2nc(N)c(N(C)C)c(Cl)n2)c1F]

4,6-Dichloro-2-(4-chloro-2-fluoro-3-methoxyphenyl)-5-methoxy-pyrimidine (500 mg, 1.5 mmol) was suspended in ammonia saturated ethanol (10 mL) and heated in a CEM microwave at 125° C. for 30 min The mixture was poured into 15 mL water and extracted with ethyl acetate thrice. The combined organic phases were washed once with brine, dried and evaporated to give the title compound (420 mg, 88% yield: $^1$H NMR (DMSO-d$_6$) δ 7.59 (dd, 1H), 7.45 (br s, 2H), 7.39 (dd, 1H), 3.91 (s, 3H), 3.76 (s, 3H).

Another compound prepared by the procedures of Example 17 is:

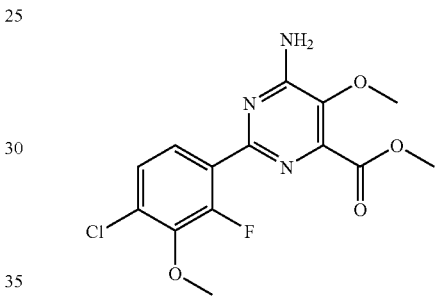

6-Chloro-2-(4-chloro-2-fluoro-3-methoxyphenyl)-N$^5$,N$^5$-dimethyl-pyrimidine-4,5-diamine: $^1$H NMR (CDCl$_3$) δ 7.60 (dd, 1H), 1.20 (dd, 1H), 4.01 (s, 3H), 2.81 (s, 6H).

18. Preparation of 6-Amino-2-(4-chloro-2-fluoro-3-methoxyphenyl)-5-methoxypyrimidine-4-carboxylic acid methyl ester

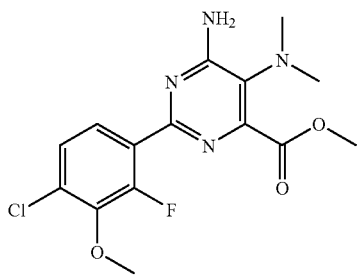 [SMILES: COC(=O)c1nc(-c2ccc(Cl)c(OC)c2F)nc(N)c1N(C)C]

6-Chloro-2-(4-chloro-2-fluoro-3-methoxyphenyl)-5-methoxy-pyrimidin-4-ylamine (300 mg, 0.94 mmol), triethylamine (0.26 mL, 190 mg, 1.9 mmol), palladium acetate (11 mg, 0.05 mmol) and DPPB (43 mg, 0.1 mmol) were combined in 15 mL dry methanol in a 45 mL pressure reactor. The reactor was purged four times with carbon monoxide, pressurized to 300 psi with carbon monoxide, and heated to 125° C. for 18 h. The volatiles were removed under vacuum and the residue taken up in ethyl acetate and water. The organic phase was washed with water, washed with brine, dried and evaporated. The residue was purified by flash chromatography on silica gel (10-20% ethyl acetate in hexanes) to give the title compound (150 mg, 47% yield): mp 155-158° C. $^1$H NMR (CDCl$_3$): δ 7.58 (dd, 1H), 7.20 (dd, 1H), 5.56 (br s, 2H) 4.00 (s, 3H), 3.99 (d, 3H), 3.94 (s, 3H).

Another compound prepared by the procedures of Example 18 is:

6-Amino-2-(4-chloro-2-fluoro-3-methoxyphenyl)-5-dimethyl aminopyrimidine-4-carboxylic acid methyl ester (Compound 17): $^1$H NMR (CDCl$_3$) δ 7.56 (dd, 1H), 7.19 (dd, 1H), 5.67 (br s, 2H), 3.99 (s, 3H), 3.98 (s, 3H), 2.74 (s, 6H).

19. Preparation of 2-(4-Chloro-2-fluoro-3-methoxyphenyl)-5-ethoxy-6-hydroxypyrimidine-4-carboxylic acid methyl ester

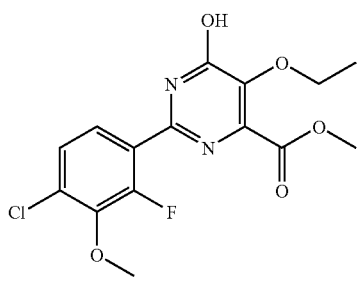 [SMILES: CCOc1c(O)nc(-c2ccc(Cl)c(OC)c2F)nc1C(=O)OC]

Sodium methoxide (12 mL, 62.74 mmol) was added dropwise to a solution of 2-ethoxy-3-oxo-succinic acid diethyl ester (9.7 g of 75% purity, 31.37 mol), 4-chloro-2-fluoro-3-methoxybenzamidine hydrochloride (5 g, 20.91 mol) and MeOH (24 mL). The reaction was allowed to stir for 1 hour. The reaction was cooled to 0° C. and 1 N HCl was added to acidify the reaction. The reaction was extracted with ethyl acetate thrice. The organic extracts were combined, washed with brine, dried, filtered and concentrated. The product was purified by flash chromatography on silica gel (0-50% EtOAc/hexane) the recrystallized from dichloromethane/hexane to give a white solid (623 mg, 8% yield): mp 173-175° C.: $^1$H NMR (CDCl$_3$) δ 11.28 (br s, 1H), 7.78 (dd, 1H), 7.31 (dd, 1H), 4.35 (q, 2H), 4.02 (s, 3H), 3.98 (s, 3H), 1.38 (t, 3H).

20. Preparation of 6-Chloro-2-(4-chloro-2-fluoro-3-methoxyphenyl)-5-ethoxy-pyrimidine-4-carboxylic acid

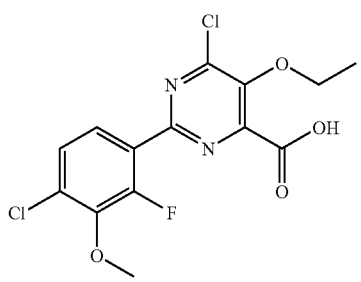 [SMILES: CCOc1c(Cl)nc(-c2ccc(Cl)c(OC)c2F)nc1C(=O)O]

A slurry of 2-(4-chloro-2-fluoro-3-methoxyphenyl)-5-ethoxy-6-hydroxypyrimidine-4-carboxylic acid methyl ester (560 mg, 1.6 mmol) was prepared in 7.8 mL of methanol. 2M aqueous sodium hydroxide (3.1 mL, 6.3 mmol) was added and the resulting nearly homogeneous tan solution was stirred at ambient temperature for 2 h. The reaction mixture was acidified to pH 4 via dropwise addition of concentrated hydrochloric acid and the solvents were removed by rotary evaporation. The crude product was slurried in water, vacuum filtered, and dried under vacuum to produce 420 mg (78% yield) of the desired intermediate product. Ethyl acetate (3.0 mL) was then added to this intermediate followed by DMF (10 μL, 0.12 mmol) and thionyl chloride (400 μL, 5.1 mmol). The reaction mixture was then sealed and heated at 70° C. for 8 h. Water (6 mL) was then added to the cooled reaction mixture and it was stirred for 30 min at ambient temperature. The reaction mixture was then poured into a 125 mL separatory funnel containing 50 mL 0.1M hydrochloric acid and extracted with ethyl acetate three times. The organic layers were combined, dried, filtered and concentrated to afford the title compound (440 mg, 99% yield): $^1$H NMR (DMSO-d$_6$) δ 7.76 (dd, 1H, J=8, 9 Hz), 7.48 (dd, 1H, J=2, 9 Hz), 4.22 (q, 2H, J=7 Hz), 3.94 (d, 3H, J=1 Hz), 1.37 (t, 3H, J=7 Hz).

21. Preparation of 6-Amino-2-(4-chloro-2-fluoro-3-methoxyphenyl)-5-ethoxy-pyrimidine-4-carboxylic acid (Compound 18)

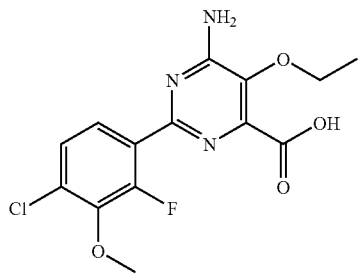 [SMILES: CCOc1c(N)nc(-c2ccc(Cl)c(OC)c2F)nc1C(=O)O]

6-Chloro-2-(4-chloro-2-fluoro-3-methoxyphenyl)-5-ethoxy-pyrimidine-4-carboxylic acid (380 mg, 1.1 mmol) was slurried in water (3.5 mL) and 28% aqueous ammonium hydroxide solution (720 μL, 10.6 mmol) was added. The reaction mixture was sealed and heated at 80° C. for 24 h. The reaction mixture was then acidified to pH 7 via dropwise addition of concentrated hydrochloric acid, and the crude product transferred into a 500 mL separatory funnel containing 100 mL 0.1M hydrochloric acid solution. The product was then extracted with dichloromethane five times. The combined organic layers were then dried, filtered and concentrated to yield the title compound (250 mg, 69% yield) as a tan solid: $^1$H NMR (DMSO-d$_6$) δ 7.58 (dd, 1H, J=8, 9 Hz), 7.38 (dd, 1H, J=2, 9 Hz), 3.98 (q, 2H, J=7 Hz), 3.90 (d, 3H, J=1 Hz), 1.31 (t, 3H, J=7 Hz).

22. Preparation of 6-Amino-2-(4-chloro-2-fluoro-3-methoxyphenyl)-5-methylsulfanylpyrimidine-4-carboxylic acid methyl ester (Compound 19)

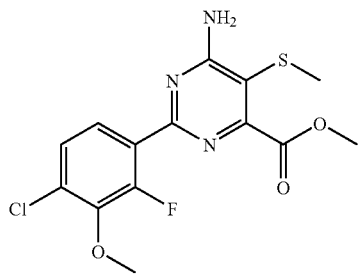 [SMILES: COC(=O)c1nc(-c2ccc(Cl)c(OC)c2F)nc(N)c1SC]

6-Amino-5-bromo-2-(4-chloro-2-fluoro-3-methoxyphenyl)-pyrimidine-4-carboxylic acid (830 mg, 2.2 mmol; see WO 2007/082076 A1 for preparation) was combined with sodium methanthiolate (470 mg, 6.7 mmol) and cuprous iodide (1.6 g, 8.3 mmol) in 12 mL dry DMF and heated to 50° C. After heating for 4 h, the mixture was cooled, taken up in water and ethyl acetate and acidified with 2M HCl. A small amount of solid was removed by filtration and the separated aqueous phase was extracted again with ethyl acetate. The combined organic phases were washed twice with water, washed once with brine, dried and evaporated. The crude product was dissolved in 7 mL THF and 5 L methanol and treated with 1.5 mL of 2.0M (trimethylsilyl)diazomethane and stirred at room temperature for 30 min A few drops of acetic acid were added to destroy excess reagent. The reaction solution was heated briefly to reflux and then concentrated. The product was purified by flash chromatography on silica gel (ethyl acetate/hexane gradient with 2% acetic acid) to yield the title compound (100 mg, 12.7% yield): $^1$H NMR (CDCl$_3$): δ 7.65 (m, 1H), 7.23 (m, 1H), 5.98 (br s, 2H), 4.00 (s, 3H), 3.99 (d, 3H), 2.35 (s, 3H).

23. Preparation of 6-Amino-2-(4-chloro-2-fluoro-3-methoxyphenyl)-5-(2,2,2-trifluoroethoxy)pyrimidine-4-carboxylic acid methyl ester (Compound 20)

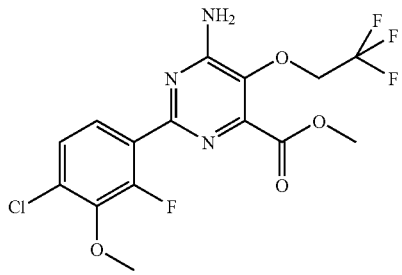 [SMILES: COC(=O)c1nc(-c2ccc(Cl)c(OC)c2F)nc(N)c1OCC(F)(F)F]

6-Amino-5-bromo-2-(4-chloro-2-fluoro-3-methoxyphenyl)-pyrimidine-4-carboxylic acid (240 mg, 0.64 mmol), 2,2,2-trifluoroethanol (1.4 mL, 1.9 g, 1.9 mmol), cesium carbonate (1.0 g, 3.2 mmol) and cuprous bromide (92 mg, 0.64 mmol) were combined in 7 mL dry DMF and heated to 80° C. for 3 h. After cooling, the mixture was diluted with water and extracted twice with ethyl acetate. The combined extracts were washed twice with water, dried and evaporated. The residue was purified by flash chromatography on silica gel (5 to 20% ethyl acetate in hexane) and then repurified by preparative HPLC (55% acetonitrile buffered with 0.1% v/v acetic acid). The purified acid was taken up in 5 mL methanol, treated with a 2 M solution of (trimethylsilyl)diazomethane in hexanes (1 mL) and stirred for 30 m at 25° C. The excess reagent was destroyed by addition of 0.5 mL acetic acid and the volatiles were removed by evaporation. The residue was taken up in ethyl acetate, washed with saturated sodium bicarbonate, washed with brine, dried and evaporated. The residue was taken up in a small amount of dichloromethane and the product was precipitated as a solid by slow addition of hexane to give 32 mg of the title compound as a white solid: mp 123-125° C.: $^1$H NMR (CDCl$_3$) δ 7.61 (dd, 1H), 7.20 (dd, 1H), 5.51 (br s, 2H), 4.51 (q, 1H), 4.01 (s, 3H), 3.99 (s, 3H).

24. Preparation of 6-Amino-2-(4-chloro-2-fluoro-3-methoxyphenyl)-5-methylsulfanyl-pyrimidine-4-carboxylic acid (Compound 21)

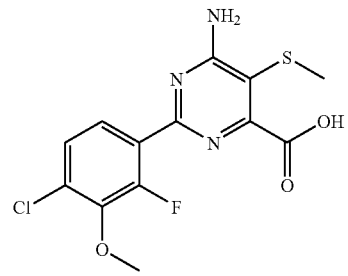 [SMILES: COc1c(Cl)ccc(-c2nc(N)c(SC)c(C(=O)O)n2)c1F]

6-amino-2-(4-chloro-2-fluoro-3-methoxyphenyl)-5-methylsulfanyl-pyrimidine-4-carboxylic acid methyl ester (100 mg, 0.28 mmol) was dissolved in 2 mL methanol and 0.5 mL of 2N sodium hydroxide (1 mmol) was added. The reaction mixture was stirred at room temperature for 4 h and then acidified with a slight excess of 2N HCl. The resulting solution was concentrated and partitioned between ethyl acetate and water. The organic phase was dried and concentrated to yield the title compound (68 mg, 70% yield): mp 153° C. (dec.): $^1$H NMR (CDCl$_3$): δ 7.63 (m, 1H), 7.2 (m, 1H), 6.4 (br s, 2H), 3.98 (s, 3H), 2.42 (s, 3H).

Other compounds prepared by the procedure of Example 24 are:

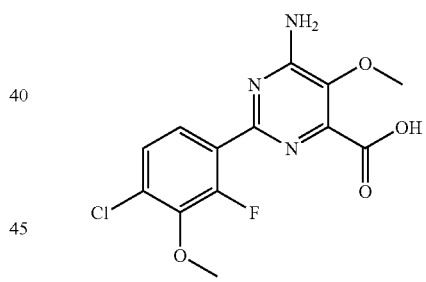

6-Amino-2-(4-chloro-2-fluoro-3-methoxyphenyl)-5-methoxypyrimidine-4-carboxylic acid (Compound 22): $^1$H NMR (DMSO-d$_6$) δ 7.58 (dd, 1H), 7.38 (dd, 1H), 7.35 br s, 2H), 3.91 (s, 3H), 3.76 (s, 3H).

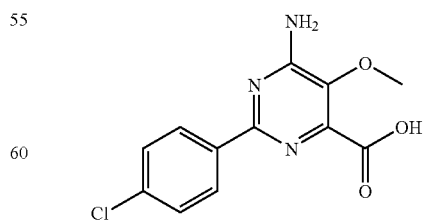

6-Amino-2-(4-chlorophenyl)-5-methoxypyrimidine-4-carboxylic acid (Compound 23): $^1$H NMR (DMSO-d$_6$) δ 8.21 (d, 2H), 7.49 (d, 2H), 7.33 (br s, 2H), 3.72 (s, 3H).

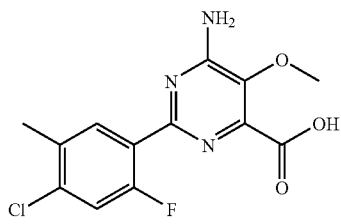 [SMILES: COc1c(N)nc(-c2cc(C)c(Cl)cc2F)nc1C(=O)O]

6-Amino-2-(4-chloro-2-fluoro-5-methylphenyl)-5-methoxypyrimidine-4-carboxylic acid (Compound 24): $^1$H NMR (DMSO-d$_6$) δ 7.79 (d, 2H), 7.42 (d, 2H), 7.37 (br s, 2H), 3.73 (s, 3H), 2.32 (s, 3H).

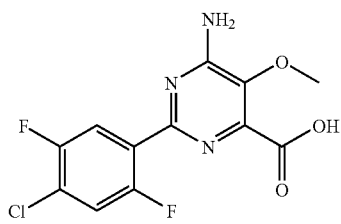

6-Amino-2-(4-chloro-2,5-difluorophenyl)-5-methoxypyrimidine-4-carboxylic acid (Compound 25): $^1$H NMR (DMSO-d$_6$) δ 7.82 (d, 1H), 7.69 (dd, 1H), 7.41 (br s, 2H), 3.73 (s, 3H).

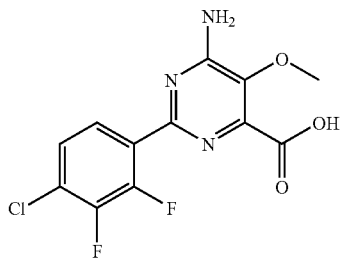 [SMILES: COc1c(N)nc(-c2ccc(Cl)c(F)c2F)nc1C(=O)O]

6-Amino-2-(4-chloro-2,3-difluorophenyl)-5-methoxypyrimidine-4-carboxylic acid (Compound 26): $^1$H NMR (DMSO-d$_6$) δ 7.72 (m, 1H), 7.49 (m, 1H), 7.40 (br s, 2H), 3.76 (s, 3H).

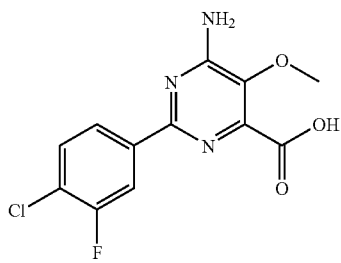 [SMILES: COc1c(N)nc(-c2ccc(Cl)c(F)c2)nc1C(=O)O]

6-Amino-2-(4-chloro-3-fluorophenyl)-5-methoxypyrimidine-4-carboxylic acid (Compound 27): $^1$H NMR (DMSO-d$_6$) δ 3.76 (s, 3H), 7.40 (bs, 2H), 7.69 (t, J=8.09 Hz, 1H), 8.07-8.12 (m, 1H).

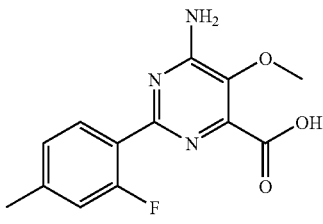 [SMILES: COc1c(N)nc(-c2ccc(C)cc2F)nc1C(=O)O]

6-Amino-2-(2-fluoro-4-methylphenyl)-5-methoxypyrimidine-4-carboxylic acid (Compound 28): $^1$H NMR (DMSO-d$_6$) δ 2.35 (s, 3H), 3.75 (bs, 2H), 7.07 (d, J=9.85 Hz, 1H), 7.28 (bs, 2H) 7.72 (t, 1H, J=8.09 Hz).

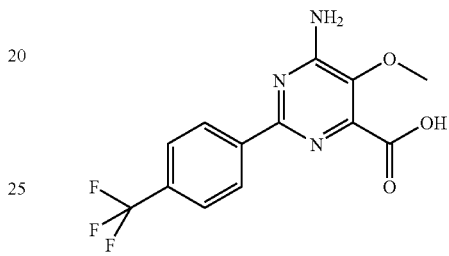

6-Amino-5-methoxy-2-(4-trifluoromethylphenyl)pyrimidine-4-carboxylic acid (Compound 29): $^1$H NMR (DMSO-d$_6$) δ 3.77 (s, 3H), 7.41 (bs, 2H), 7.83 (d, J=8.34 Hz, 1H), 8.43 (d, 1H, J=8.34 Hz).

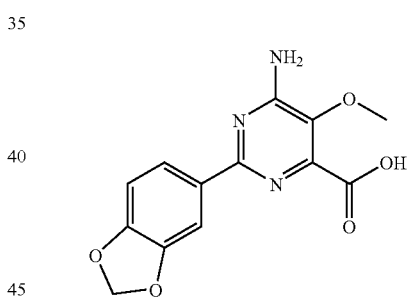

6-Amino-2-benzo[1,3]dioxol-5-yl-5-methoxypyrimidine-4-carboxylic acid (Compound 30): $^1$H NMR (DMSO-d$_6$) δ 3.70 (s, 3H), 6.05 (s, 2H), 6.95 (d, J=8.24 Hz, 1H), 7.21 (bs, 2H), 7.67 (d, 1H, J=1.65 Hz) 7.81 (dd, 1H, J=1.66 Hz).

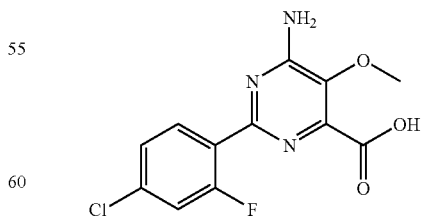

6-Amino-2-(4-chloro-2-fluorophenyl)-5-methoxypyrimidine-4-carboxylic acid (Compound 31): $^1$H NMR (DMSO-d$_6$) δ 7.86 (dd, 1H, J=8, 9 Hz), 7.50 (dd, 1H, J=2, 9 Hz), 7.37 (dd, 1H, J=2, 8 Hz), 3.75 (s, 3H).

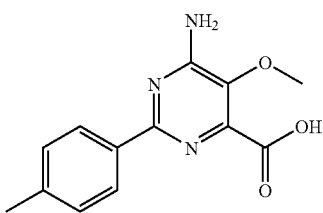 [SMILES: COc1c(N)nc(-c2ccc(C)cc2)nc1C(=O)O]

6-Amino-5-methoxy-2-p-tolylpyrimidine-4-carboxylic acid (Compound 32): $^1$H NMR (DMSO-d$_6$) δ 8.12 (br d, 2H, J=8 Hz), 7.16-7.32 (m, 4H), 3.73 (s, 3H), 2.35 (s, 3H).

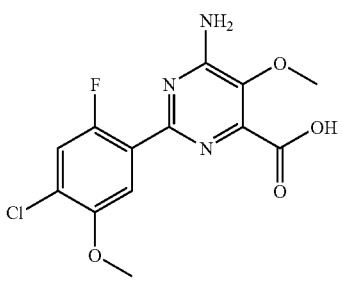 [SMILES: COc1cc(-c2nc(N)c(OC)c(C(=O)O)n2)c(F)cc1Cl]

6-Amino-2-(4-chloro-2-fluoro-5-methoxyphenyl)-5-methoxypyrimidine-4-carboxylic acid (Compound 33): $^1$H NMR (DMSO-d$_6$) δ 7.31-7.56 (m, 4H), 3.88 (s, 3H), 3.75 (s, 3H).

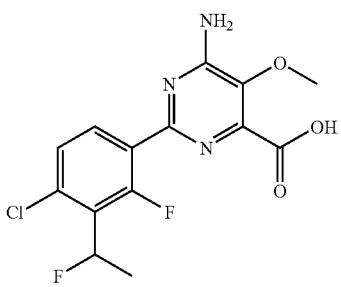 [SMILES: COc1c(N)nc(-c2ccc(Cl)c(C(C)F)c2F)nc1C(=O)O]

6-Amino-2-[4-chloro-2-fluoro-3-(1-fluoroethyl)phenyl]-5-methoxypyrimidine-4-carboxylic acid (Compound 34): $^1$H NMR (DMSO-d$_6$) δ 7.81 (t, 1H, J=8 Hz), 7.20-7.50 (m, 3H), 6.05-6.28 (m, 1H), 3.75 (s, 3H), 1.73 (dd, 3H, J=7, 23 Hz).

25. Preparation of 2-(4-Chloro-2-fluoro-3-methoxyphenyl)-6-methoxy-7-methyl-7H-purine

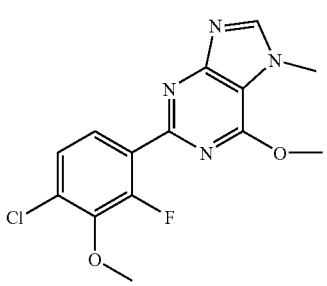 [SMILES: COc1c(Cl)ccc(-c2nc(OC)c3c(ncn3C)n2)c1F]

2-Chloro-6-methoxy-7-methyl-7H-purine (1.2 g, 6.0 mmol, see Monatshefte fuer Chemie (1985), 116(3), 341-51 for preparation), 2-(4-chloro-2-fluoro-3-methoxyphenyl)-4,4,5,5-tetramethyl-[1,3,2]dioxaborolane (2.1 g, 8.6 mmol), Pd(PPh$_3$)$_2$Cl$_2$ (300 mg, 0.42 mmol) and cesium fluoride (1.6 g, 11 mmol) were combined in 10 mL dry, deaerated acetonitrile and heated to reflux. After 2 h, the mixture was cooled and mixed with ethyl acetate and water. The organic phase was washed with water, brine, dried and evaporated under vacuum. The residue was purified by flash chromatography on silica gel with 20% ethyl acetate/hexane to give the title compound (1.3 g, 67% yield: mp 191-192° C.: $^1$H NMR (CDCl$_3$) δ 8.0 (s, 1H), 7.90 (dd, 1H), 7.22 (dd, 1H), 4.22 (s, 3H), 4.08 (s, 3H), 4.02 (s, 3H).

26. Preparation of 6-Chloro-2-(4-chloro-2-fluoro-3-methoxyphenyl)-7-methyl-7H-purine

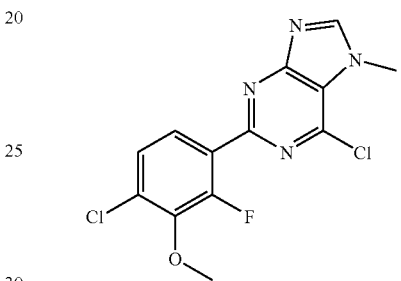

2-(4-Chloro-2-fluoro-3-methoxyphenyl)-6-methoxy-7-methyl-7H-purine (1.0 g, 3.1 mmol) was combined with 10 mL 6M HCl and heated at reflux for 2 h. After cooling, the mixture was diluted with 15 mL water and the pH was adjusted to 2 by addition of 2M aqueous sodium hydroxide. The precipitated material was collected by filtration, washed with water and dried under vacuum at 80° C. A 500 mg sample of the crude intermediate was slurried in chloroform (10 mL), treated with DMF (0.62 mL, 580 mg, 8.0 mmol) and then with thionyl chloride (0.58 mL, 950 mg, 8.0 mmol). The mixture was heated at reflux for 3 h, cooled and poured into 20 mL of ice-water. The pH was adjusted to 10 by addition of 1M sodium hydroxide. The precipitated product was taken up in ethyl acetate, washed twice with water, once with brine, dried and evaporated to give the title compound (500 mg, 49% yield over two steps): mp 184-186° C.: $^1$H NMR (DMSO-d$_6$) δ 8.8 (s, 1H), 7.8 (dd, 1H), 7.46 (dd, 1H), 4.11 (s, 3H), 3.96 (s, 3H).

27. Preparation of 2-(4-Chloro-2-fluoro-3-methoxyphenyl)-7-methyl-7H-purine-6-carboxylic acid methyl ester

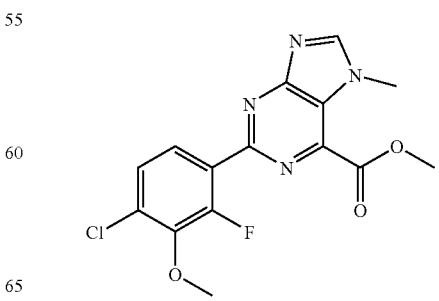

6-Chloro-2-(4-chloro-2-fluoro-3-methoxyphenyl)-7-methyl-7H-purine (400 mg, 1.2 mmol), Pd(OAc)$_2$ (13 mg, 0.058 mmol), DPPB (51 mg, 0.12 mmol) and triethylamine (0.18 mL, 130 mg, 1.3 mmol) were combined in 20 mL dry methanol in a 45 mL pressure reactor. The reactor was purged and pressured to 300 psi with carbon monoxide and heated to 115° C. for 18 h. The volatiles were removed under vacuum and the residue was taken up in ethyl acetate and water. The organic phase was dried and evaporated; and the residue was purified by preparative HPLC (70% acetonitrile buffered with 0.1% v/v acetic acid) to provide the title compound (280 mg, 66% yield): mp 197-198° C.: $^1$H NMR (DMSO-d$_6$) δ 8.88 (s, 1H), 7.81 (dd, 1H), 7.48 (dd, 1H), 4.04 (s, 3H), 4.03 (s, 3H), 3.96 (s, 3H).

28. Preparation of 6-Amino-2-(4-chloro-2-fluoro-3-methoxyphenyl)-5-methylaminopyrimidine-4-carboxylic acid (Compound 35)

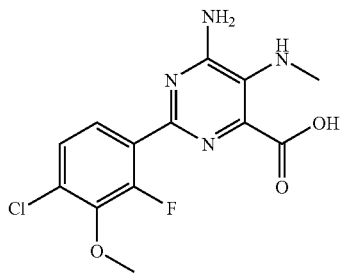 [SMILES: CNc1c(N)nc(-c2ccc(Cl)c(OC)c2F)nc1C(=O)O]

2-(4-Chloro-2-fluoro-3-methoxyphenyl)-7-methyl-7H-purine-6-carboxylic acid methyl ester (200 mg, 0.57 mmol) was slurried in 2M sodium hydroxide (10 mL) and heated at reflux for 2 h. After cooling, the pH was adjusted to 4 with 1M HCl. The precipitated solid was dissolved by shaking the mixture with two portions of ethyl acetate (45 mL each). The combined organic phases were washed with brine, dried and evaporated to give the title compound (100 mg, 53% yield): $^1$H NMR (DMSO-d$_6$) δ 7.62 (dd, 1H), 7.36 (dd, 1H), 7.05 (br s, 2H), 3.97 (m, 1H), 3.91 (s, 3H), 2.17 (s, 3H).

29. Preparation of Herbicidal Compositions

In the following illustrative compositions, parts and percentages are by weight.

Emulsifiable Concentrates

| Formulation A | WT % |
|---|---|
| Compound 1 | 26.2 |
| Polyglycol 26-3 | 5.2 |
| Nonionic emulsifier-(di-sec-butyl)-phenyl-poly(oxypropylene)block polymer with (oxyethylene). The polyoxyethelene content is about 12 moles. | |
| Witconate P12-20 (Anionic emulsifier-calcium dodecylbenzene sulfonate-60 wt. % active) | 5.2 |
| Aromatic 100 (Xylene range aromatic solvent) | 63.4 |

| Formulation B | WT % |
|---|---|
| Compound 2 | 3.5 |
| Sunspray 11N (paraffin oil) | 40.0 |
| Polyglycol 26-3 | 19.0 |
| Oleic acid | 1.0 |
| Xylene range aromatic solvent | 36.5 |

| Formulation C | WT % |
|---|---|
| Compound 5 | 13.2 |
| Stepon C-65 | 25.7 |
| Ethomeen T/25 | 7.7 |
| Ethomeen T/15 | 18.0 |
| Xylene range aromatic solvent | 35.4 |

| Formulation D | WT % |
|---|---|
| Compound 12 | 30.0 |
| Agrimer A1-10LC (emulsifier) | 3.0 |
| N-methyl-2-pyrrolidone | 67.0 |

| Formulation E | WT % |
|---|---|
| Compound 13 | 10.0 |
| Agrimul 70-A (dispersant) | 2.0 |
| Amsul DMAP 60 (thickener) | 2.0 |
| Emulsogen M (emulsifier) | 8.0 |
| Attagel 50 (suspension aid) | 2.0 |
| Crop oil | 76.0 |

These concentrates can be diluted with water to give emulsions of suitable concentrations for controlling weeds.

Wettable Powders

| Formulation F | WT % |
|---|---|
| Compound 18 | 26.0 |
| Polyglycol 26-3 | 2.0 |
| Polyfon H | 4.0 |
| Zeosyl 100 (Precipitated hydrated SiO$_2$) | 17.0 |
| Barden clay + inerts | 51.0 |

| Formulation G | |
|---|---|
| | WT % |
| Compound 21 | 62.4 |
| Polyfon H (sodium salt of lignin sulfonate) | 6.0 |
| Sellogen HR (sodium naphthalene sulfonate) | 4.0 |
| Zeosyl 100 | 27.6 |

| Formulation H | |
|---|---|
| | WT % |
| Compound 23 | 1.4 |
| Kunigel V1 (carrier) | 30.0 |
| Stepanol ME Dry (wetter) | 2.0 |
| Tosnanon GR 31A (binder) | 2.0 |
| Kaolin NK-300 Clay (filler) | 64.6 |

The active ingredient is applied to the corresponding carriers and then these are mixed and ground to yield wettable powders of excellent wettability and suspension power. By diluting these wettable powders with water it is possible to obtain suspensions of suitable concentrations for controlling weeds.

Water Dispersible Granules

| Formulation I | |
|---|---|
| | WT % |
| Compound 22 | 26.0 |
| Sellogen HR | 4.0 |
| Polyfon H | 5.0 |
| Zeosyl 100 | 17.0 |
| Kaolinite clay | 48.0 |

The active ingredient is added to the hydrated silica, which is then mixed with the other ingredients and ground to a powder. The powder is agglomerated with water and sieved to provide granules in the range of −10 to +60 mesh. By dispersing these granules in water it is possible to obtain suspensions of suitable concentrations for controlling weeds.

Granules

| Formulation J | |
|---|---|
| | WT % |
| Compound 25 | 5.0 |
| Celetom MP-88 | 95.0 |

The active ingredient is applied in a polar solvent such as N-methylpyrrollidinone, cyclohexanone, gamma-butyrolactone, etc. to the Celetom MP 88 carrier or to other suitable carriers. The resulting granules can be applied by hand, granule applicator, airplane, etc. in order to control weeds.

| Formulation K | |
|---|---|
| | WT % |
| Compound 27 | 1.0 |
| Polyfon H | 8.0 |
| Nekal BA 77 | 2.0 |
| Zinc Stearate | 2.0 |
| Barden Clay | 87.0 |

All materials are blended and ground to a powder then water is added and the clay mixture is stirred until a paste is formed. The mixture is extruded through a die to provide granules of proper size.

30. Evaluation of General Postemergence Herbicidal Activity

Seeds or nutlets of the desired test plant species were planted in Sun Gro MetroMix® 360 planting mixture, which typically has a pH of 6.0 to 6.8 and an organic matter content of about 30 percent, in plastic pots with a surface area of 64 square centimeters. When required to ensure good germination and healthy plants, a fungicide treatment and/or other chemical or physical treatment was applied. The plants were grown for 7-21 days in a greenhouse with an approximate 15 hour photoperiod which was maintained at about 23-29° C. during the day and 22-28° C. during the night. Nutrients and water were added on a regular basis and supplemental lighting was provided with overhead metal halide 1000-Watt lamps as necessary. The plants were employed for testing when they reached the first or second true leaf stage.

A weighed amount, determined by the highest rate to be tested, of each test compound was dissolved in 4 mL of a 97:3 v/v (volume/volume) mixture of acetone and dimethyl sulfoxide (DMSO) to obtain concentrated stock solutions. If the test compound did not dissolve readily, the mixture was warmed and/or sonicated. The concentrated stock solutions obtained were diluted with 20 mL of an aqueous mixture containing acetone, water, isopropyl alcohol, DMSO, Atplus 411F crop oil concentrate, and Triton® X-155 surfactant in a 48.5:39:10:1.5:1.0:0.02 v/v ratio to obtain spray solutions containing the highest application rates. Additional application rates were obtained by serial dilution of 12 mL of the high rate solution into a solution containing 2 mL of 97:3 v/v (volume/volume) mixture of acetone and dimethyl sulfoxide (DMSO) and 10 mL of an aqueous mixture containing acetone, water, isopropyl alcohol, DMSO, Atplus 411F crop oil concentrate, and Triton X-155 surfactant in a 48.5:39:10:1.5:1.0:0.02 v/v ratio to obtain ½×, ¼×, ⅛× and ¹⁄₁₆× rates of the high rate. Compound requirements are based upon a 12 mL application volume at a rate of 187 L/ha. Formulated compounds were applied to the plant material with an overhead Mandel track sprayer equipped with a 8002E nozzles calibrated to deliver 187 L/ha over an application area of 0.503 square meters at a spray height of 18 inches (43 cm) above the average plant canopy height. Control plants were sprayed in the same manner with the solvent blank.

The treated plants and control plants were placed in a greenhouse as described above and watered by sub-irrigation to prevent wash-off of the test compounds. After 14 days, the condition of the test plants as compared with that of the untreated plants was determined visually and scored on a scale of 0 to 100 percent where 0 corresponds to no injury and 100 corresponds to complete kill.

Some of the compounds tested, application rates employed, plant species tested, and results are given in Table 1.

TABLE 1

Post-emergent Weed Control

| Compound | Rate g ai/ha | % Growth Reduction | | | |
|---|---|---|---|---|---|
| | | ABUTH | POLCO | SETFA | ECHCG |
| 1 | 140 | 100 | 100 | 95 | 100 |
| 2 | 140 | 98 | 100 | 70 | 50 |
| 3 | 280 | 60 | 85 | 0 | 0 |
| 9 | 140 | 95 | 100 | 30 | 90 |
| 10 | 140 | 100 | 90 | 0 | 10 |
| 11 | 140 | 90 | 85 | 0 | 85 |
| 12 | 140 | 50 | 80 | 90 | 85 |
| 13 | 140 | 100 | 100 | 35 | 0 |
| 14 | 140 | 100 | 100 | 100 | 100 |
| 16 | 140 | 60 | 100 | 10 | 0 |
| 18 | 280 | 70 | 100 | 70 | ND |
| 19 | 195 | 90 | 100 | 85 | 90 |
| 21 | 140 | 85 | 100 | 60 | 100 |
| 22 | 140 | 100 | 100 | 100 | 100 |
| 31 | 140 | 100 | 100 | 70 | 85 |
| 32 | 140 | 80 | 100 | 65 | 95 |

ND—Not determined
ABUTH - Velvetleaf (*Abutilon theophrasti*)
POLCO - Wild buckwheat (*Polygonum convolvulus*)
SETFA - Giant foxtail (*Setaria faberi*)
ECHCG - Barnyardgrass (*Echinochloa crus-galli*)

What is claimed is:

1. A compound of the formula XIV

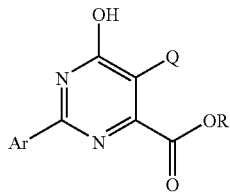

XIV wherein
Q represents an alkoxy, haloalkoxy, thioalkoxy, halothioalkoxy, alkylamino or haloalkylamino;
R represents alkyl;
Ar represents a phenyl group substituted with three substituents selected from halogen, nitro, cyano, formyl, $C_1$-$C_6$ alkyl, $C_2$-$C_6$ alkenyl, $C_2$-$C_6$ alkynyl, $C_1$-$C_6$ alkoxy, $C_2$-$C_4$ alkoxyalkyl, $C_2$-$C_6$ alkylcarbonyl, $C_1$-$C_6$ alkylthio, $C_1$-$C_6$ alkylsulfinyl, $C_1$-$C_6$ alkylsulfonyl, $C_2$-$C_4$ alkenyloxy, $C_2$-$C_4$ alkynloxy, $C_2$-$C_4$ alkenylthio, $C_2$-$C_4$ alkynylthio, $C_1$-$C_6$ haloalkyl, $C_2$-$C_6$ haloalkenyl, $C_2$-$C_6$ haloalkynyl, $C_1$-$C_6$ haloalkoxy, $C_2$-$C_4$ haloalkoxyalkyl, $C_2$-$C_6$ haloalkylcarbonyl, $C_1$-$C_6$ haloalkythio, $C_1$-$C_6$ haloalkylsulfinyl, $C_1$-$C_6$ haloalkylsulfonyl, $C_3$-$C_6$ trialkylsilyl, $C_2$-$C_4$ haloalkenyloxy, $C_2$-$C_4$ haloalkynyloxy, $C_2$-$C_4$ haloalkenylthio, $C_2$-$C_4$ haloalkynylthio, —OCH$_2$CH$_2$—, —OCH$_2$CH$_2$CH$_2$—, —OCH$_2$O—, —OCH$_2$CH$_2$O—, —C(O)OR$_4$, —C(O)NR$_3$R$_4$, —CR$_3$NOR$_4$, —NR$_3$R$_4$, —NR$_3$OR$_4$, —NR$_3$SO$_2$R$_4$, —NR$_3$C(O)R$_4$, —NR$_3$C(O)OR$_4$, —NR$_3$C(O)NR$_3$R$_4$ or —NCR$_3$NR$_3$R$_4$,;
R$_3$ represents H, $C_1$-$C_4$ alkyl or $C_1$-$C_4$ haloalkyl; and
R$_4$ represents $C_1$-$C_4$ alkyl or $C_1$-$C_4$ haloalkyl.

2. The compound of claim 1, wherein the Ar is selected from halogen or $C_{1-6}$ alkoxy.

3. The compound of claim 1, wherein Q is alkoxy.

4. The compound of claim 1, wherein R is methyl.

5. The compound of claim 1, wherein the compound is:

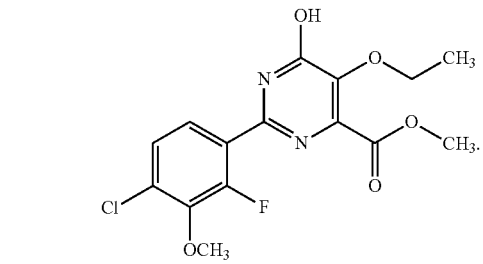 [SMILES: CCOc1c(O)nc(-c2ccc(Cl)c(OC)c2F)nc1C(=O)OC]

* * * * *